(12) United States Patent
Williams

(10) Patent No.: US 8,652,071 B2
(45) Date of Patent: Feb. 18, 2014

(54) SYSTEMS, DEVICES, AND METHODS FOR INTERPRETING MOVEMENT

(75) Inventor: Mark E. Williams, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 23 days.

(21) Appl. No.: 13/177,144

(22) Filed: Jul. 6, 2011

(65) Prior Publication Data

US 2011/0264010 A1  Oct. 27, 2011

Related U.S. Application Data

(63) Continuation of application No. 11/420,039, filed on May 24, 2006, now Pat. No. 8,007,450, which is a continuation of application No. PCT/US2006/016626, filed on May 2, 2006.

(60) Provisional application No. 60/676,924, filed on May 2, 2005.

(51) Int. Cl.
*A61B 5/103* (2006.01)

(52) U.S. Cl.
USPC .......................................................... 600/595

(58) Field of Classification Search
USPC .......................................................... 600/595
See application file for complete search history.

(56) References Cited

U.S. PATENT DOCUMENTS

| 4,836,218 | A | * | 6/1989 | Gay et al. | 600/586 |
|---|---|---|---|---|---|
| 5,441,047 | A | * | 8/1995 | David et al. | 600/483 |
| 2005/0085700 | A1 | * | 4/2005 | Sharp et al. | 600/300 |
| 2006/0195050 | A1 | * | 8/2006 | Alwan et al. | 600/595 |

OTHER PUBLICATIONS

Lechner et al. "Gait Deviations in Patients with Juvenile Rheumatoid Arthritis" Journal of American Physical Therapy 1987, p. 1335-1341.*

* cited by examiner

*Primary Examiner* — Max Hindenburg
*Assistant Examiner* — Renee Danega
(74) *Attorney, Agent, or Firm* — Shook, Hardy & Bacon; Robert J. Decker

(57) ABSTRACT

According to some exemplary embodiments, a method or system can involve associating a plurality of biokinetographic comparison results with a first specific dysfunction from a group of specific dysfunctions, each of the biokinetographic comparison results obtained from a comparison of a biokinetographic value to a standard for a corresponding biokinetographic variable.

9 Claims, 33 Drawing Sheets

4000
FAST FOURIER TRANSFORMATION RIGHT LEG

FAST FOURIER TRANSFORMATION LEFT LEG

DORSAL SPINAL COLUMN DISEASE SHOWING FOOT SLAPPING (HIGH PEAKED AMPLITUDES)

RIGHT PERONEAL NERVE INJURY (FOOT DROP) SHOWING ABRUPT TOE OFF AND PREMATURE TOE STRIKE. NOTE ASYMMETRY OF LEFT AND RIGHT AMPLITUDES

LEFT SPASTIC HEMIPARESIS SHOWING GAIT ASYMMETRY AND PELVIC ROCKING

SACRAL TRACING OF A PATIENT WITH SEVERE PERIPHERAL
NEUROPATHY SHOWING EXAGGERATED PELVIC TILT WITH >0.2 G
VARIATION BETWEEN STEPS

HIGHLIGHT OF 2800-3200 INTERVAL ABOVE SHOWING DRAMATIC
DIFFERENCE IN STEP VARIATION

NORMAL TURN AROUND

DORSAL SPINAL COLUMN DISEASE SHOWING FOOT SLAPPING (HIGH PEAKED AMPLITUDES)

SYSTEMS, DEVICES, AND METHODS FOR INTERPRETING MOVEMENT

CROSS REFERENCE TO RELATED APPLICATIONS

This application is a continuation under 35 U.S.C. §120 of U.S. patent application Ser. No. 11/420,039 filed on May 24, 2006 which claims priority under 35 U.S.C. §§120 and 363 to PCT/US06/16626 filed on May 2, 2006, which claims priority under U.S.C. §119(e) to U.S. Provisional Patent Application Ser. No. 60/676,924, filed on May 2, 2005, the entirety of each of the aforementioned applications is hereby incorporated by reference in their entirety.

BACKGROUND

Motion is a fundamental principle. And, it is a fundamental aspect of life. By way of example, the quickening fetal movement can be the first clear sign to the expectant mother that she carries new life. And, at the other extreme of the life course, terminal illness is often heralded by progressive immobility. Patterns of human movement can change throughout life from the uncertain steps of the toddler, to the insecure swagger of the adolescent, to the self-assured gait of responsible adulthood, and the progressive unsteadiness of geriatric frailty.

For human beings, motion can be a window bridging our inner and outer lives. Our movements on the purely physical plane can have resonance within our inner being and reality. Likewise our inner state can be mirrored through our movements: the springing gait of optimism, the fine tremor of anxiety, or the slow shuffle of dejection. Our motions also can affect and reflect our health status. In addition, immobility can increase our risk of diseases such as osteoporosis, heart disease, stroke, diabetes mellitus, and possibly malignancy. Alterations in movement can result from anatomic changes (perhaps influenced by genetics), illness factors, environmental conditions, and lifestyle circumstances including obesity, nutritional factors, and psycho-behavioral factors such as anxiety and depression.

The interpretation of movement can play an essential role in the clinical practice of numerous medical specialties (e.g., pediatrics, sports medicine, geriatrics, physical medicine and rehabilitation, neurology, rheumatology, orthopedics, and several others). However, these motion-based assessments are often communicated as subjective clinical impressions by an expert observer. Attempts to more fully explicate what the clinician perceives often have captured very little of the extraordinary breadth of sensory information that is being processed during these expert evaluations. Accurate, precise motion data can provide significantly deeper insights into an individual's affective, cognitive, and physical performance status.

BRIEF DESCRIPTION OF THE DRAWINGS

A wide variety of potential practical and useful embodiments will be more readily understood through the following detailed description of certain exemplary embodiments, with reference to the accompanying exemplary drawings in which.

DETAILED DESCRIPTION

Figure 1:
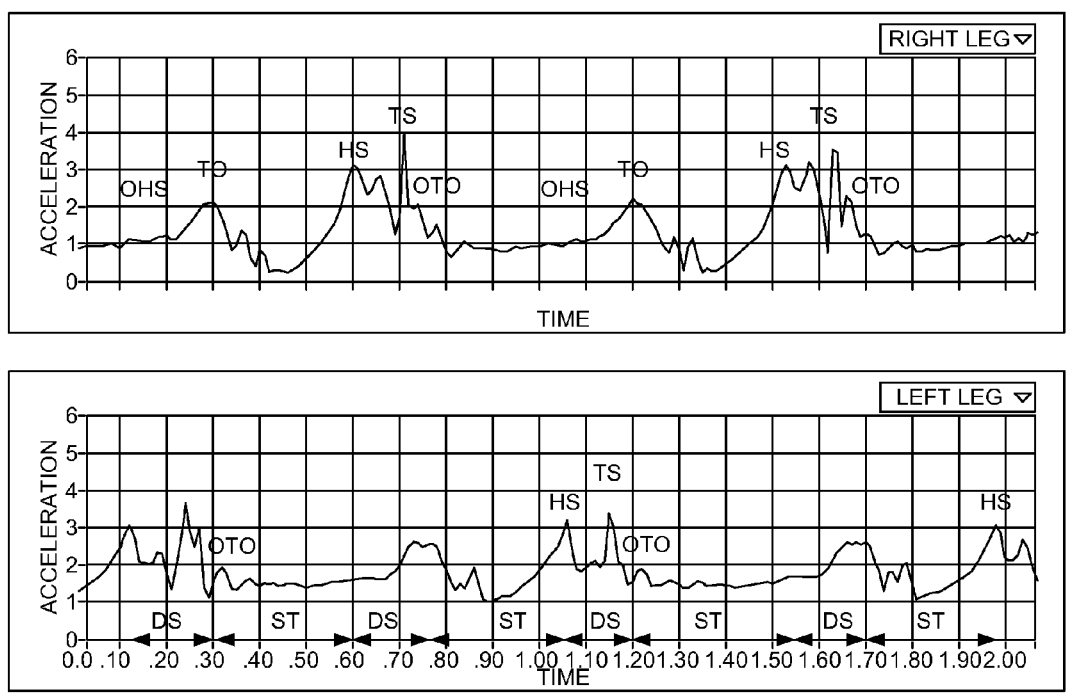
FIG. 1 is an exemplary set of biokinetographs 1000.

There can be a need for systems, devices, and methods for interpreting movement of a subject, such as, e.g., a human subject.

According to some illustrative embodiments, a method is performed and/or a system is provided that includes: automatically associating a plurality of biokinetographic comparison results with a first specific dysfunction from a group of specific dysfunctions comprising: Parkinson's disease, hemiparesis, cerebellar disease, frontal lobe disease, low pressure hydrocephalus, spinal stenosis, arthritis, orthopedic pain, orthopedic injury, motor neuropathy, and myopathy, each of the biokinetographic comparison results obtained from an automatic comparison of a biokinetographic value to a standard for a corresponding biokinetographic variable, each biokinetographic value automatically determined from a biokinetographic data set comprising a plurality of scalar sums of acceleration values in each of three orthogonal directions, each scalar sum corresponding to a particular point in time. In some examples, the method and/or system further comprises obtaining the biokinetographic data set. In some examples, the method further and/or system comprises for each biokinetographic variable, determining a biokinetographic value from the biokinetographic data set. In some other examples, the method and/or system further comprises each biokinetographic value to the standard for the corresponding biokinetographic variable. In some examples, the method and/or system includes rendering the biokinetographic data, and in some examples, the method includes rendering the plurality of biokinetographic comparison results. In some examples, the method and/or system further includes diagnosing the first specific dysfunction. In some examples, the method and/or system further includes assessing the first specific dysfunction. In some examples, the method and/or system further includes determining a treatment for the first specific dysfunction. In some examples, the method and/or system further includes providing a prognosis regarding the first specific dysfunction. In some examples, the method and/or system further includes predicting a likelihood of falling. In some examples, the method and/or system further includes identifying a second specific biokinetographic pattern. In some examples, the method and/or system further includes associating the second specific biokinetographic pattern with a second specific dysfunction. In some examples, the method and/or system further includes assessing the second specific dysfunction. In some examples, the method and/or system further includes assessing an overall health status based on the plurality of biokinetographic comparison results.

In some examples, the first specific dysfunction is Parkinson's disease, hemiparesis, cerebellar disease, frontal lobe disease, low pressure hydrocephalus, spinal stenosis, orthopedic pain, orthopedic injury, motor neuropathy, myopathy, and/or a psychological dysfunction.

In some examples, the method and/or system includes that data for the biokinetographic data set is generated by: a plurality of sensors adapted to sense different moving parts of a subject; a recording device adapted to acquire motion data generated from the plurality of sensors when the subject moves; a memory which stores the motion data acquired by the recording device; and a processor configured to convert the motion data into biokinetographic data. In some examples, the method and/or system includes that the conversion of the motion data into biokinetographic data comprises graphing the scalar sums of acceleration from each sensor over time.

According to some embodiments, a system for detecting and analyzing the motion of a subject is provided that can include: a plurality of sensors adapted to sense different moving parts of a subject; a recording device adapted to acquire motion data generated from the plurality of sensors when the subject moves; a memory which stores the motion data acquired by the recording device; and a processor configured to convert the motion data into biokinetographic data. In some examples, the sensors include biokinetic motion detectors. In some examples, the biokinetic motion detectors include tri-axial piezo-resistive accelerometers. In some examples, the system is configured such that the subject wears a plurality of sensors on the wrists, neck, sacrum, and/or ankles while generating motion data. In some examples, sensors worn on wrists and ankles by the subject are attached by straps or other equivalent means. In some examples, the plurality of sensors communicate with the recording device via wires or other equivalent means. In some examples, the recording device is supported upon the subject with a strap or other equivalent means. In some examples, the recording device acquires motion data from the plurality of sensors by wireless or other remote means. In some examples, the motion data is stored in individual channels of the memory. In some examples, the memory includes a memory card, a chip, a magnetic storage device, or an equivalent storage device. In some examples, the biokinetographic data is in the format of waveforms or waveform images.

According to some embodiments, a machine-readable medium is provided comprising machine instructions for activities comprising: automatically associating a plurality of biokinetographic comparison results with a first specific dysfunction from a group of specific dysfunctions comprising: Parkinson's disease, hemiparesis, cerebellar disease, frontal lobe disease, low pressure hydrocephalus, spinal stenosis, arthritis, orthopedic pain, orthopedic injury, motor neuropathy, and myopathy, each of the biokinetographic comparison results obtained from an automatic comparison of a biokinetographic value to a standard for a corresponding biokinetographic variable, each biokinetographic value automatically determined from a biokinetographic data set comprising a plurality of scalar sums of acceleration values in each of three orthogonal directions, each scalar sum corresponding to a particular point in time.

According to some embodiments, a signal embodied in an electromagnetic wave is provided, the signal adapted to cause an information device to: automatically associate a plurality of biokinetographic comparison results with a first specific dysfunction from a group of specific dysfunctions comprising: Parkinson's disease, hemiparesis, cerebellar disease, frontal lobe disease, low pressure hydrocephalus, spinal stenosis, arthritis, orthopedic pain, orthopedic injury, motor neuropathy, and myopathy, each of the biokinetographic comparison results obtained from an automatic comparison of a biokinetographic value to a standard for a corresponding biokinetographic variable, each biokinetographic value automatically determined from a biokinetographic data set comprising a plurality of scalar sums of acceleration values in each of three orthogonal directions, each scalar sum corresponding to a particular point in time.

According to some embodiments, a method is performed and/or a system is provided that includes: automatically: obtaining biokinetographic data; analyzing the biokinetographic data; and identifying a first specific biokinetographic pattern; and associating the first specific biokinetographic pattern with a first specific dysfunction from a group of specific dysfunctions comprising: Parkinson's disease, hemiparesis, cerebellar disease, frontal lobe disease, low pressure hydrocephalus, spinal stenosis, arthritis, orthopedic pain, orthopedic injury, motor neuropathy, and myopathy.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

Certain exemplary embodiments can conveniently and/or unobtrusively assess overall health status and/or well being of a subject, as well as specific physical and/or mental illnesses by way of a characteristic visual image (the biokinetograph) and/or a quantitative biokinetic index. Certain exemplary embodiments can enable healthcare providers to accurately interpret biokinetographic images (velocities and/or accelerations over time—examples of which are provided herein) of certain desired and/or critical body parts such as the head, trunk, and/or extremities, as movement image patterns reflective of specific conditions in health and/or illness.

By way of example, an older person's upper extremity dexterity can be intimately associated with that person's ability to live independently. Individuals who are quick and efficient in manual performance typically are at low risk for needing future help while inefficient manual performance can suggest increased risk of disability, social limitation, and increased use of health services.

Certain exemplary embodiments can relate to a motion-capture system and/or method that can enable non-invasive and/or continuous motion data collection for a large number of subjects over an extended period of time. Sensors distributed across the body at points of interest can gather, store and/or transmit data regarding position, orientation, velocity, acceleration, jerk, pulse, and/or torque, etc., among other variables, which can be manipulated and/or processed remotely for motion analysis. The sensors can be chosen to be inexpensive, unobtrusive, wearable, user-friendly, and/or have a long-lifetime, etc., yet can continuously collect accurate, precise data. All types of motion on any part of the body can be collected and/or analyzed, including, but not limited to, simultaneous monitoring of movements of the head, arm, trunk, waist, and/or leg, etc. The subject can be closely monitored, so ambient and/or physiologic factors that might influence motion such as affect, cognition, and/or physical performance can be incorporated into the analysis. Biological and/or ambient monitoring systems that can help add context to the collected motion data also can be integrated.

Systematic analysis of biokinetographic images can quantify the various clinical, environmental, motivational, mental, and/or mechanical, etc., components that can be related to human movement. This novel approach can enable one to objectively map an individual's personal movement signature. This biokinetographic signature can be as unique as a fingerprint. Mental, physical, and/or emotional elements can be superimposed on this personal signature, modifying its appearance and/or reflecting visible changes in movement, such as the change in gait caused by a sprained ankle Biokinetographic profiles can be gathered longitudinally to analyze the individual's age-specific performance trajectory. This can allow the development of norms and/or biokinetographic indices for human performance, somewhat analogous to the growth charts used by pediatricians to identify children with developmental abnormalities and/or the intelligence quotients used by psychologists. Deviations from these norms can provide an early warning of functional change before disabilities become permanent and/or evident through traditional evaluations.

Various movement vector components can be influenced by neuro-muscular factors (e.g., stroke, peripheral neuropathy, foot drop, etc.), mechanical anatomic factors (e.g., previous hip fracture, osteoarthritis, amputation, etc.), psycho-behavioral conditions (e.g., anxiety, depression, etc.), any of which can affect aspects of human motion as can be detected by these sensitive devices. These factors can be of great interest with regard to their relationship to biokinetographic signatures.

Certain exemplary embodiments can provide an entirely new approach to the diagnosis of human movement in health and illness (digital biokinetographics) by analyzing and interpreting the waveform images from sensors (for example, miniature digital three-dimensional sensors) to create noninvasive, unobtrusive, and/or ultra-sensitive biomarkers of health and/or illness. Certain exemplary embodiments can identify unique movement signatures that can indicate either successful or unsuccessful integration of affective, cognitive, and/or physical performance. Analysis of these biokinetographs can result in innovative, objective measures of health, disability, early identification of pre-disease pathways, and/or new ways to monitor the effects of treatments.

Numerous clinical conditions can be associated with movement abnormalities as a characteristic and/or defining clinical feature. For example, cerebral palsy, multiple sclerosis, Parkinson's disease, stroke, Alzheimer's disease, normal pressure hydrocephalus, osteoarthritis of the knee or hip, low back pain, spinal stenosis, and/or the psycho-motor retardation associated with major depression can have movement abnormalities as characteristic features. Systematic analysis of biokinetographic tracings can identify the critical, characteristic, and/or defining features of these and/or other clinical conditions. Each clinical condition can have a unique signature from the biokinetograph. Visual feature detection can be followed by computational feature extraction and/or calculations of various diagnostic features.

Certain exemplary embodiments can comprise a hardware system of devices that can detect and/or record motion patterns, and/or a processing system that can convert the acquired motion patterns into interpretable, biokinetographic data.

The hardware system generally can include a plurality of sensors and/or a recording device. In particular, biokinetic sensors can be attached to different moving parts of the subject's body to capture the desired motion patterns. The sensors also can be connected to the recording device, which can have a memory component to store the captured motion data. In certain exemplary embodiments, the recorder can be attached to a part of the body not being tested for motion and/or free of interfering movements from other parts of the body. The recorder can store into memory the data generated from the biokinetic sensors when the subject moves.

In certain exemplary embodiments, the memory component that stores the motion data can be removable from the recording device, such as a memory chip and/or card, which can then be transferred from the recorder to a processing system, and/or otherwise can transfer data remotely or directly. Raw data can be downloaded from the memory component into the processing system, which can convert the data into the desired biokinetographic format for analysis of the subject's motion patterns.

In certain exemplary embodiments, the biokinetic sensors can be wristwatch-sized tri-axial piezo-resistive accelerometers (motion detectors) that can measure accelerations related to changes in velocity and/or gravitational acceleration. The acceleration measured can depend on the direction and/or magnitude of either and/or both types of acceleration. Subjects can wear the sensors on their wrists, neck, sacrum, each ankle and/or other body part while walking a closed course. The exact sensor numbers and/or configuration can depend on the purpose of the assessment (diagnosis, monitoring, and/or predicting disability, etc.). The accelerometers can be attached to the wrists and/or ankles by hook and loop fastener straps and/or equivalent attachment means. The biokinetic sensors can be connected by wires and/or wirelessly to the recorder (which can be the size of a cellular telephone). The recorder can be located on the patient and/or remote from the patient. The recorder can be attached to and/or around the waist with, for example, a hook and loop fastener system, belt, cord, Theraband® sash, and/or equivalent attachment means. Motion signals and/or data from each sensor can be sampled, for example, at a frequency in the range of 20 Hz to 2500 Hz, such as 25, 51, 74.9, 100, 125.3, 152, 250, 300, 500, 999, and/or 1999 Hz, etc., including all values and sub-ranges therebetween. Samples can be stored in individual channels on a memory card and/or other magnetic storage device or equivalent means in the recorder. The resulting data can be transferred into the biokinetographic analysis system.

A number of analysis techniques exploiting a variety of degrees of freedom for which measurements can be obtained from the sensors can be employed to compare gaits and/or to diagnose critical conditions. One approach involves graphing the sum of the vector magnitudes, or scalar values, of acceleration from each sensor over time to produce biokinetographic waveforms such as those illustrated in FIG. 1, which illustrates the basic components of simultaneous right and left ankle tracings of a healthy adult woman. In FIG. 1, the following annotations are used: HS=heel strike; TS=toe strike; TO=toe lift off; OHS=opposite heel strike; OTO=opposite toe lift off; DS=double stance time; ST=swing through.

Figure 2:
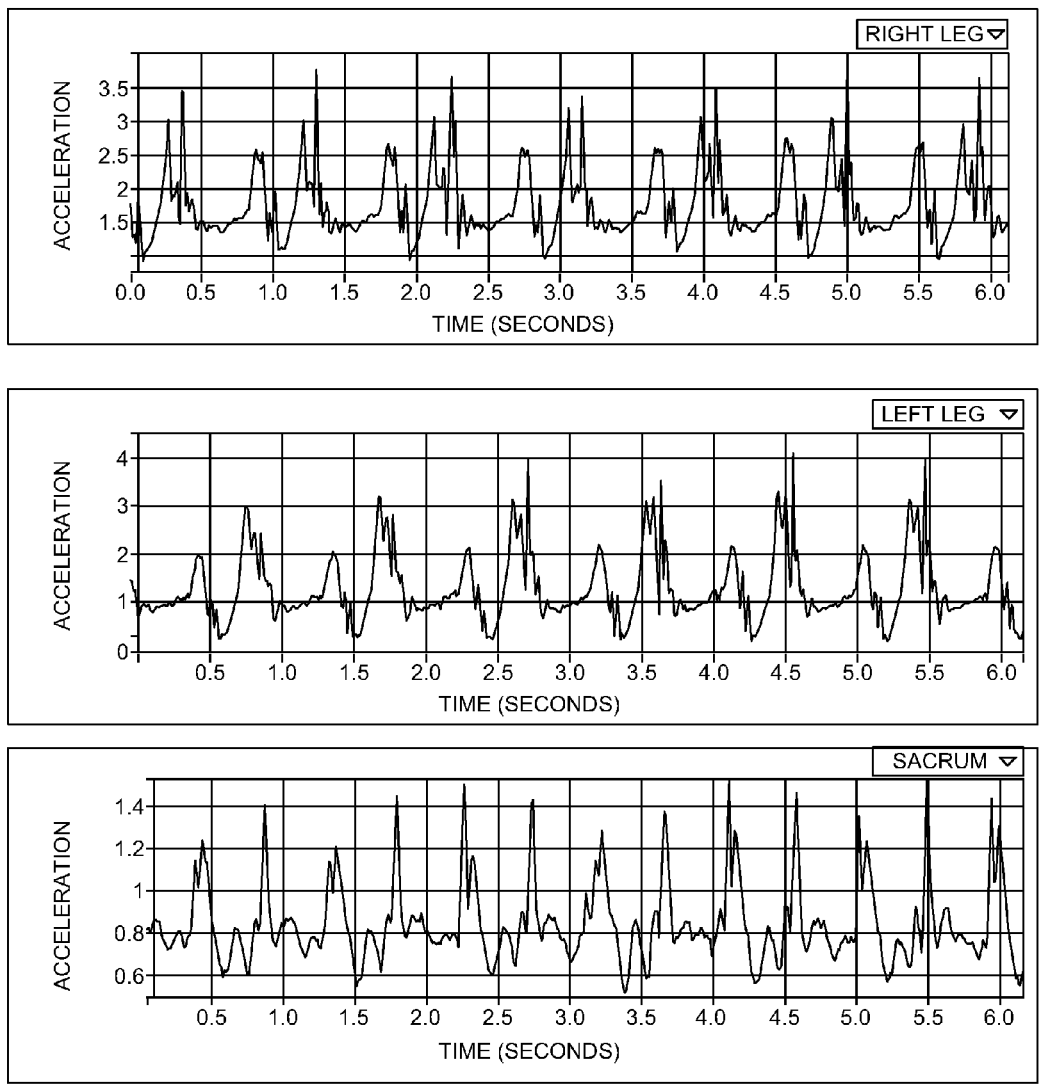
FIG. 2 is an exemplary set of biokinetographs 2000.

FIG. 2 is an exemplary set of biokinetographs 2000, which illustrates for exemplary purposes the periodic movement waveform and the gait components of the biokinetographic signature, recorded at the right ankle, left ankle, and sacrum in a healthy adult woman.

Certain exemplary embodiments can provide an analytic framework that can address any of three domains: movement biomechanics, energy expenditure, and/or navigational skill. Movement biomechanics can deal with aspects of the movement cycle including heal strike, toe strike, heal liftoff, toe liftoff, single limb phase, double limb phase, swing phase, and/or opposite heal strike, etc.; arm swing character; stability of the center of mass, and/or step symmetry (degree of stability and/or equality between left and right steps). These biomechanical elements can be readily determined from the biokinetograph. Energy expenditure can be quantified by step rate (which can be calculated as number of steps per minute); step rate variability (changes in step rate over time); magnitude of the Fast Fourier Transformation; and/or the magnitude of accelerations shown on the ordinate. Navigational parameters can include variability of ambulatory axis (degree of wobble and/or sway); uniformity of Fast Fourier Transformation pattern; and/or turning efficiency in changing direction. Combinations of biomechanical, energy conservation and/or navigational patterns for specific clinical states is shown in Table 1, which can be used to assist healthcare professionals in diagnosing such conditions.

TABLE 1

| Clinical condition | Biomechanics | Energy Conservation | Navigational Skill |
|---|---|---|---|
| Neurological conditions | | | |
| Stroke | Focal impairment* | Normal | Normal or impaired |
| Parkinson's disease | Global impairment* | Reduced* | Normal or impaired |
| Alzheimer's disease | Normal | Normal | Impaired |
| Low pressure hydrocephalus | Global impairment* | Reduced* | Impaired |
| Huntington's disease | Global impairment* | Reduced* | Impaired |
| Demyelinating disease | Global or focal* | Reduced | Impaired |
| Cerebellar disease | Global impairment* | Abnormal* | Impaired |
| Peripheral neuropathy | Focal impairment* | Abnormal* | Impaired |
| Radiculopathy | Focal impairment* | Reduced | Normal |
| Autonomic dysfunction | Normal or global* | Normal | Normal |
| Visual impairment | Normal | Normal | Impaired |
| Orthopedic conditions | | | |
| Low back pain | Global impairment* | Reduced | Normal |
| Painful hip | Focal impairment* | Normal or reduced* | Normal |
| Painful knee | Focal impairment* | Normal or reduced* | Normal |
| Painful foot or ankle | Focal impairment* | Reduced* | Normal |
| Amputation | Focal impairment* | Normal | Normal |
| Cardiovascular disease | | | |
| Heart disease | Normal or global | Reduced* | Normal |
| Peripheral vascular | Normal or Focal* | Reduced* | Normal |
| Respiratory disease | | | |
| Chronic lung disease | Normal or global | Reduced | Normal |

TABLE 1-continued

| Clinical condition | Biomechanics | Energy Conservation | Navigational Skill |
|---|---|---|---|
| Psychiatric Illnesses | | | |
| Depression | Normal or global | Reduced* | Normal |
| Anxiety | Normal or global* | Reduced* | Normal |
| Fear | Normal or global | Reduced* | Normal |
| Delirium | Global | Reduced* | Impaired |
| Geriatric Syndromes | | | |
| Dizziness | Normal | Normal | Impaired |
| Falling | Global* | Reduced* | Normal or impaired |
| Failure to thrive (frailty) | Global* | Reduced* | Normal or impaired |

*Characteristic pattern on biokinetographic tracing

A potentially fundamental feature of the analytic processing can be comparing the individual's biokinetic profile with normal patterns of movement. Normally, lower extremity movements, such as steps, can be symmetrical with prompt initiation of movement, fluid biomechanics, decisive turning and/or change of direction, adequate velocity, and/or a linear trajectory. There are typically minimal adventitious movements and/or arm swing is rhythmic. A focal abnormality on a biokinetographic tracing can relate to an abnormality on only one body part such as an ankle. Focal biokinetographic abnormalities in an extremity can suggest neurological impairment such as a stroke and/or peripheral nerve injury (foot drop and/or sciatica), and/or arthritis involving one or more joints such as the hip and/or knee. Vascular insufficiency to a limb and/or previous trauma and/or amputation also can produce focal findings. Global abnormalities can refer to impairments seen in all sensors. Systemic illnesses and/or multi-system conditions and/or primary neurological diseases can produce these patterns. Energy conservation can be normal, abnormal, reduced, and/or increased. Normal energy conservation can occur when normal amounts and/or patterns of energy are utilized. Abnormal energy conservation can relate to normal amounts of energy utilization but abnormal patterns of utilization. Reduced energy conservation can involve using less efficient approaches to movement, often with characteristic adventitious movements. Navigational skill can be normal or impaired. Impaired skill can imply non-linear inefficient movement trajectory, such as staggering and/or weaving.

ANALYTICAL EXAMPLES

Example 1

Frailty and High Fall Risk

Figure 3:
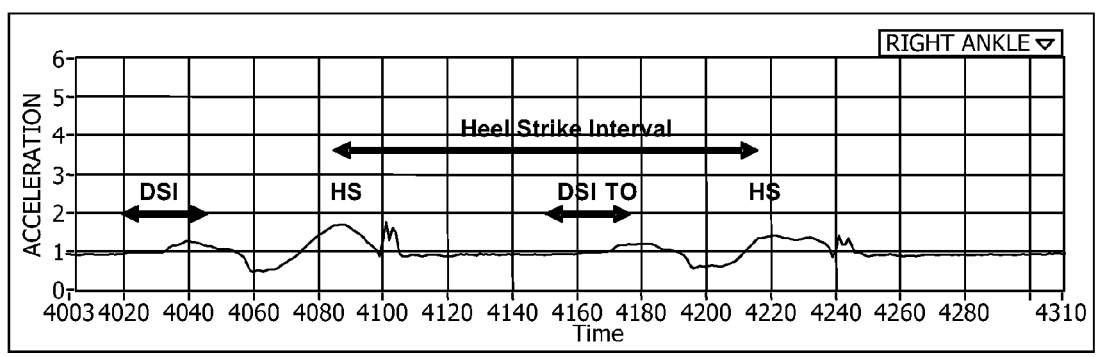
FIG. 3 is an exemplary set of biokinetographs 3000.
Figure 3:
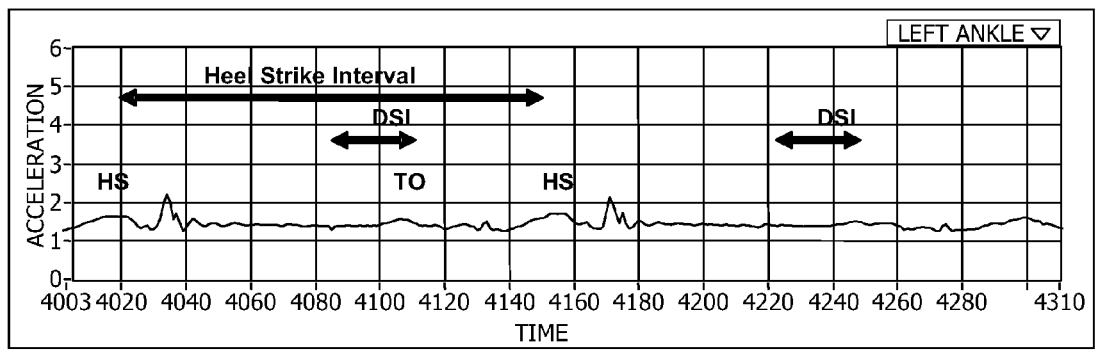

FIG. 3 is an exemplary set of biokinetographs 3000, which illustrates for exemplary purposes a simultaneous 3 second biokinetographic tracing of the right and left ankle in a frail 81 year old woman with back pain.

Figure 4:
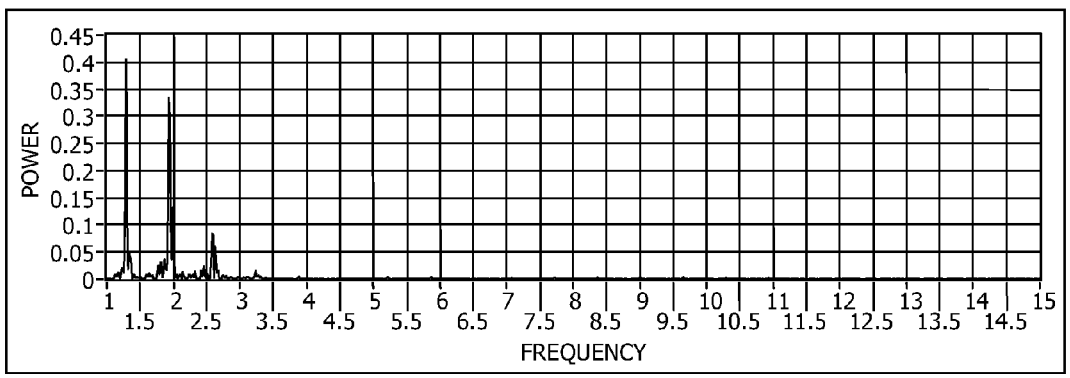
FIG. 4 is an exemplary set of biokinetographs 4000.
Figure 4:
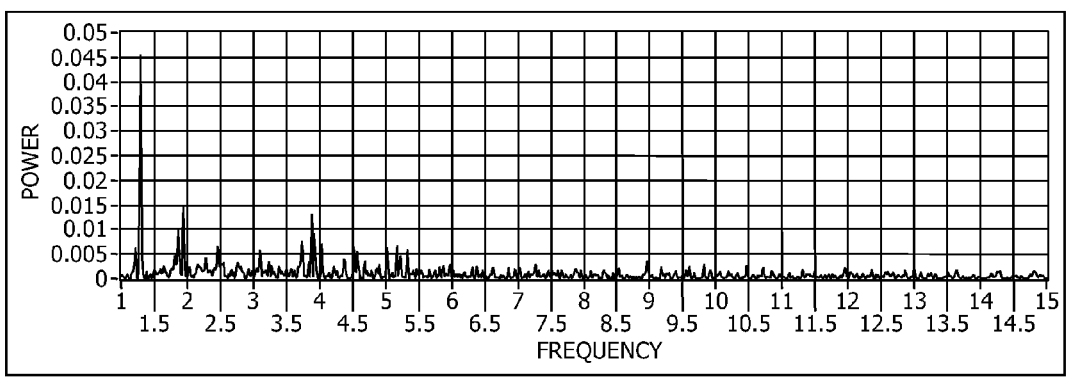

FIG. 4 is an exemplary set of biokinetographs 4000, which illustrate frequency components, as obtained via Fast Fourier Transform, corresponding to the biokinetographs 3000 of FIG. 3.

Basic Interpretation: The heel strike (HS) interval is 1350 milliseconds for each ankle which can be indicative of a slow gait (88.8 steps/min). The double stance intervals (from HS of one ankle to the toe off (TO) of the other) are symmetrical so there is no evidence of a joint, bone, muscle or nerve problem involving only one leg. The magnitude of accelerations is less than one gravitational unit for any of the waves indicative of very low energy utilization and a shuffling gait. The FFT shows relatively low power but a relatively organized gait so there is no evidence of wobbling or staggering. This data can suggest that this person is slow, frail and at high risk of falling.

Example 2

An 81 Year Old Woman with a Painful Left Foot

Figure 5:
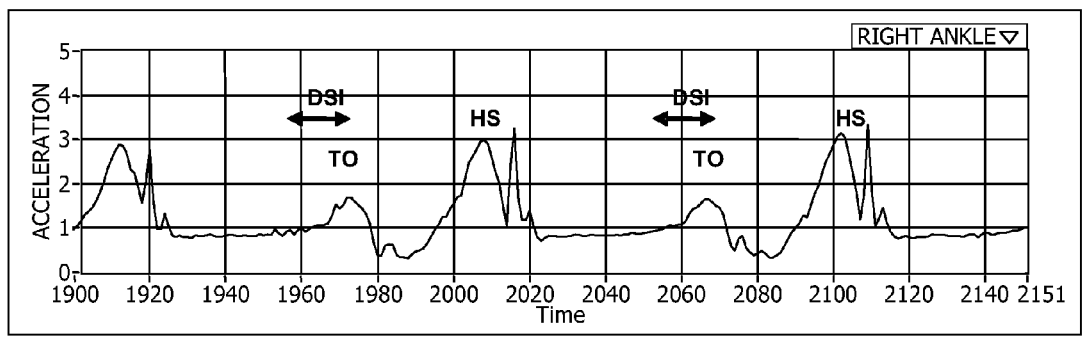
FIG. 5 is an exemplary set of biokinetographs 5000.
Figure 5:
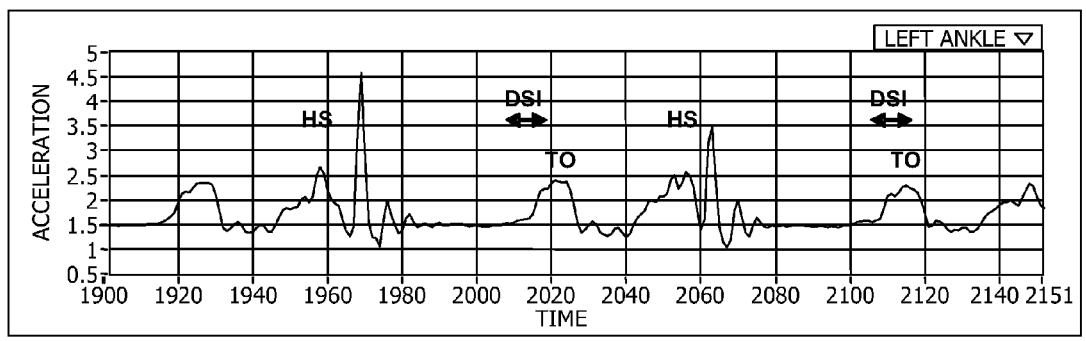

FIG. 5 is an exemplary set of biokinetographs 5000, which illustrates for exemplary purposes a simultaneous 2.5 second biokinetographic tracing of the right and left ankle in an 81 year old woman with a painful left foot.

Basic Interpretation: The heel strike interval is 950 milliseconds on the right and 980 milliseconds on the left for a normal gait (124.4 steps/min). The double stance times are 170 and 120 milliseconds, a 50 millisecond difference that suggests a local problem with the left foot. As soon as the right foot touches (HS) the left foot is ready to lift because of pain. The accelerations are brisk on the right with 2 g heel strikes, while the left heel strikes are only 1 g again suggesting pain. The left HS waveform is more jagged than the right, which can provide another clue of possible discomfort.

Example 3

Figure 6:
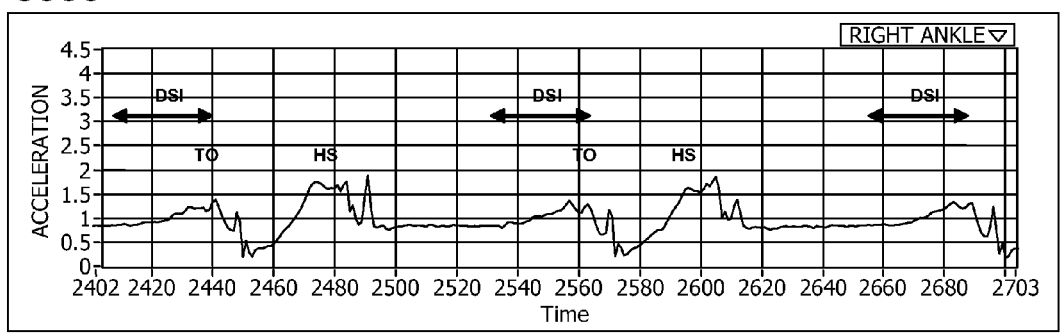
FIG. 6 is an exemplary set of biokinetographs 6000.
Figure 6:
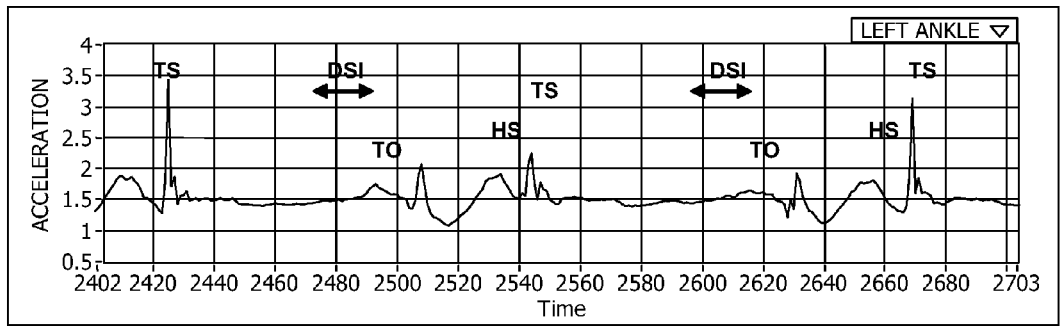

An 84 Year Old Man Who Had a Left Below the Knee Amputation 50 Years Ago and Has Severe Osteoarthritis of His Right Knee FIG. 6 is an exemplary set of biokinetographs 6000, which illustrates for exemplary purposes a simultaneous 3 second biokinetographic tracing of the right and left ankle in an 84 year old man with a previous left below the knee amputation and severe osteoarthritis of his right knee.

Basic Interpretation: The heel strike interval is 1200 milliseconds on each side for a slow symmetrical gait (100 steps/min). However, the double stance times are very asymmetric (320 milliseconds on the right and 200 on the left). The waveforms are also asymmetric and low amplitudes under one g except for the power toe strike (TS) from the prosthetic foot, which generates 1.5-2 g, over twice the amplitude of the heel strike. The amputation and prosthesis is clearly evident as is the adaptation with overall gait symmetry. The low amplitudes can suggest a high fall risk and approaching frailty.

ADDITIONAL EXAMPLES

What follows are some additional examples, in which the following convention is used: sensor 1 is always right wrist; sensor 2 is the sacrum; sensor 3 is just over the right ankle; and sensor 4 is over the left ankle.

Figure 7:
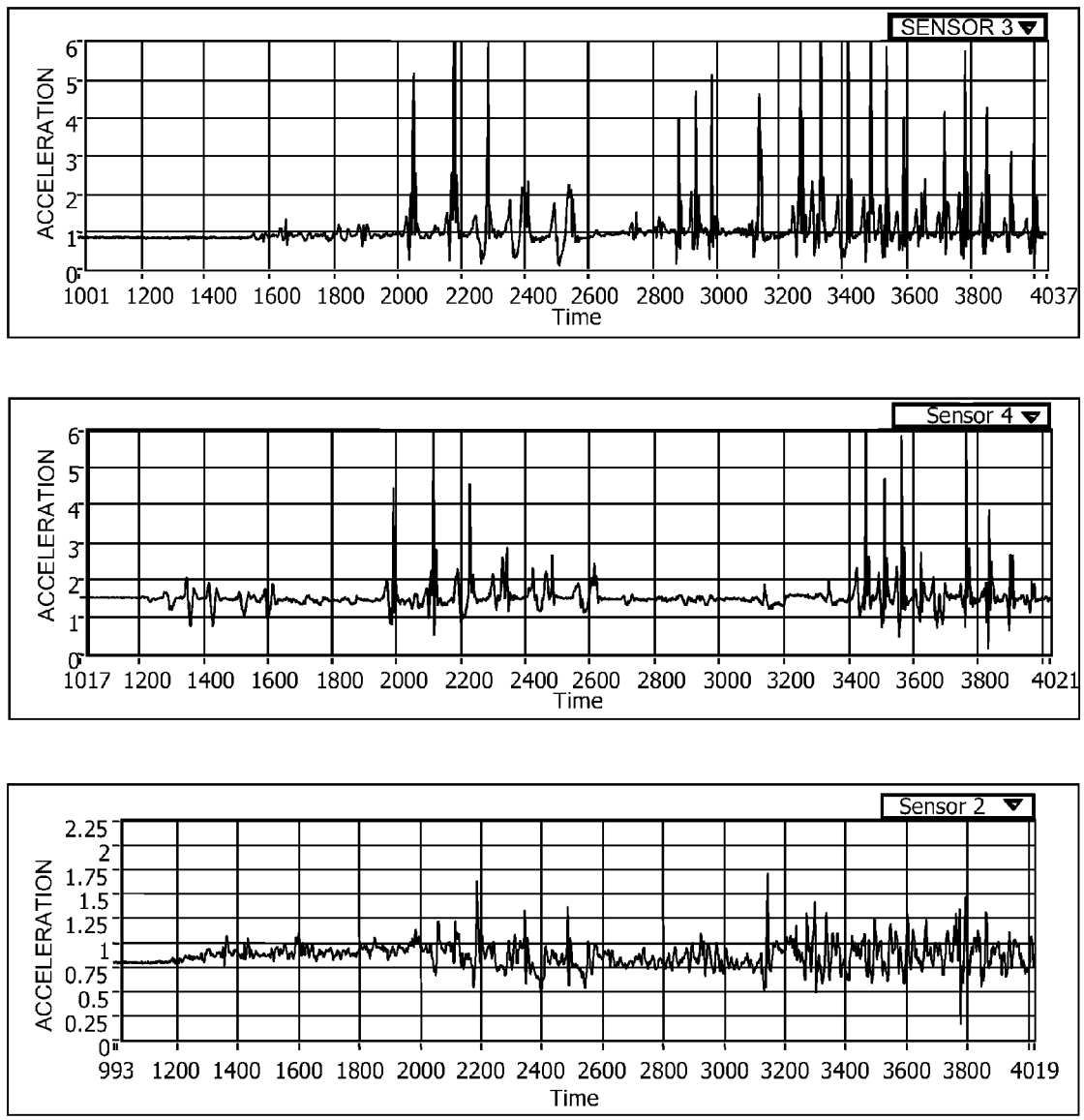
FIG. 7 is an exemplary set of biokinetographs 7000.

FIG. 7 is an exemplary set of biokinetographs illustrating Low Pressure Hydrocephalus showing freezing and tendency to normalize after a few steps.

Figure 8:
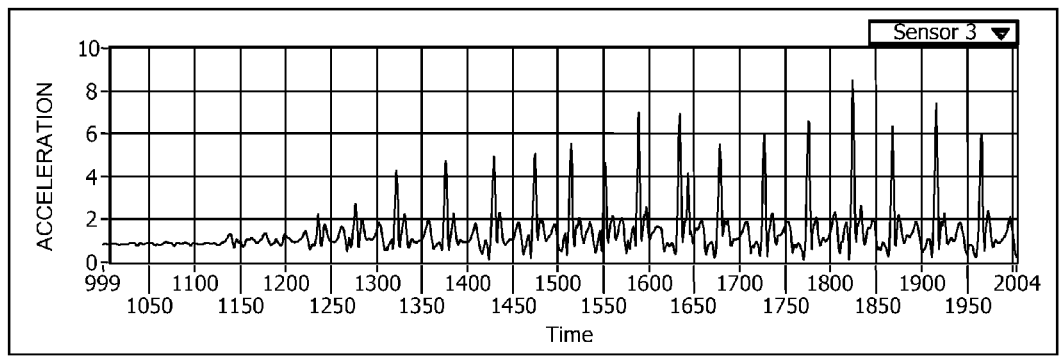
FIG. 8 is an exemplary set of biokinetographs 8000.
Figure 8:
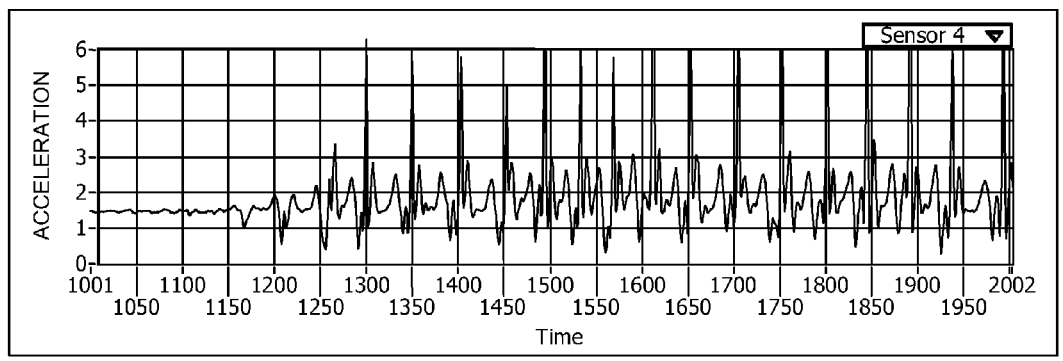
Figure 8:
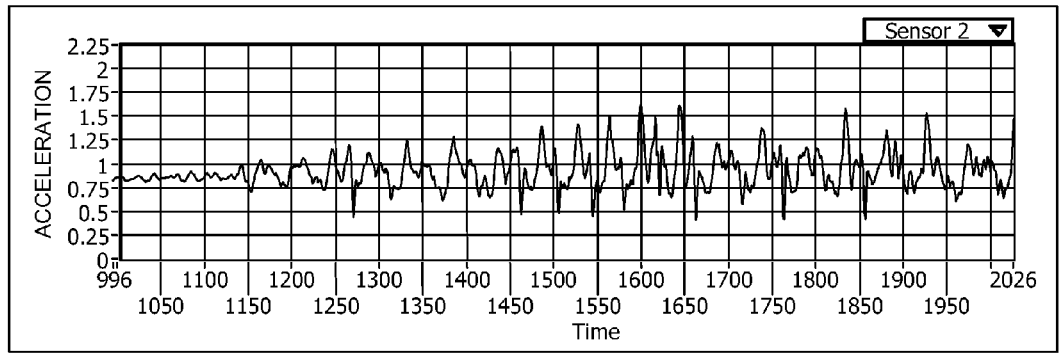

FIG. 8 is an exemplary set of biokinetographs illustrating Parkinsonism showing delay in initiation.

Figure 9:
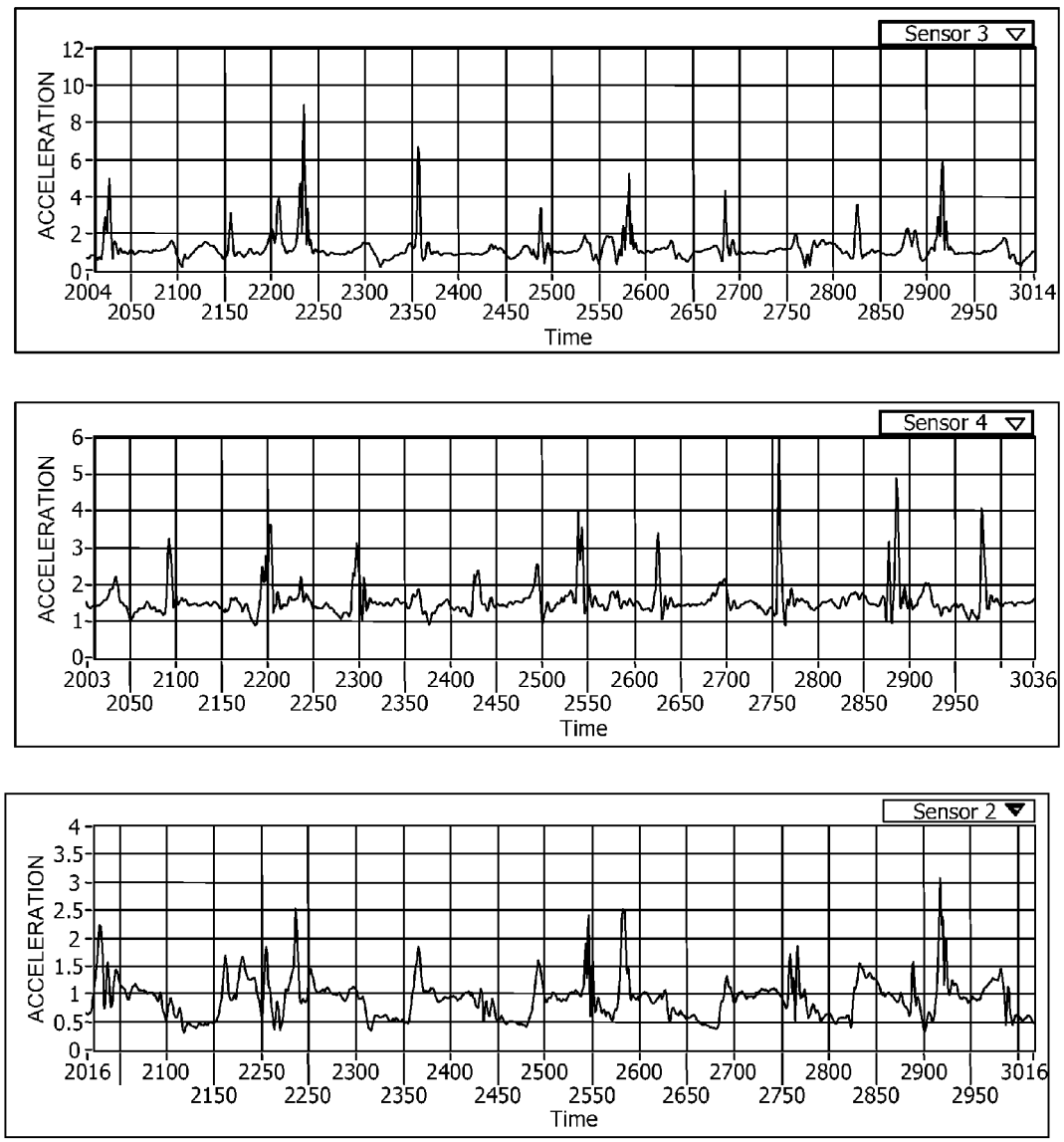
FIG. 9 is an exemplary set of biokinetographs 9000.

FIG. 9 is an exemplary set of biokinetographs illustrating cerebellar disease showing variability of amplitudes and cadence.

Figure 10:
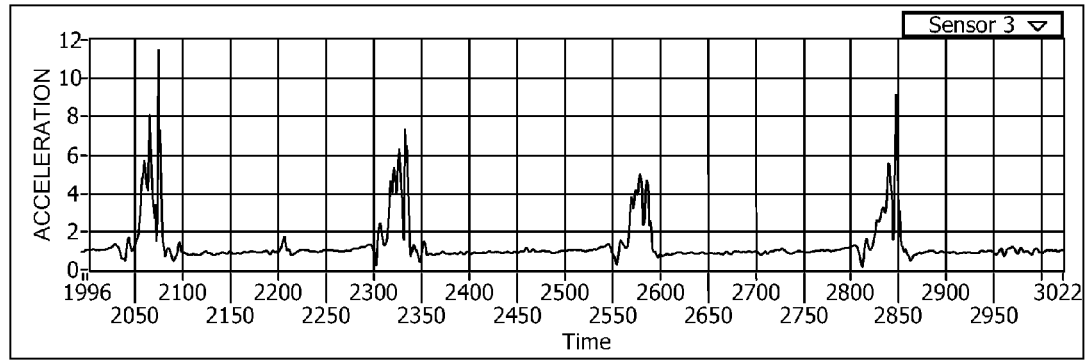
FIG. 10 is an exemplary set of biokinetographs 10000.
Figure 10:
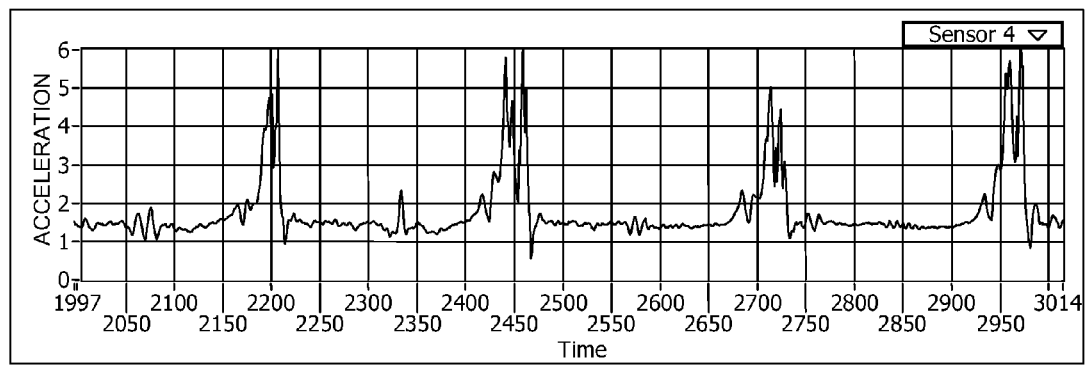
Figure 10:
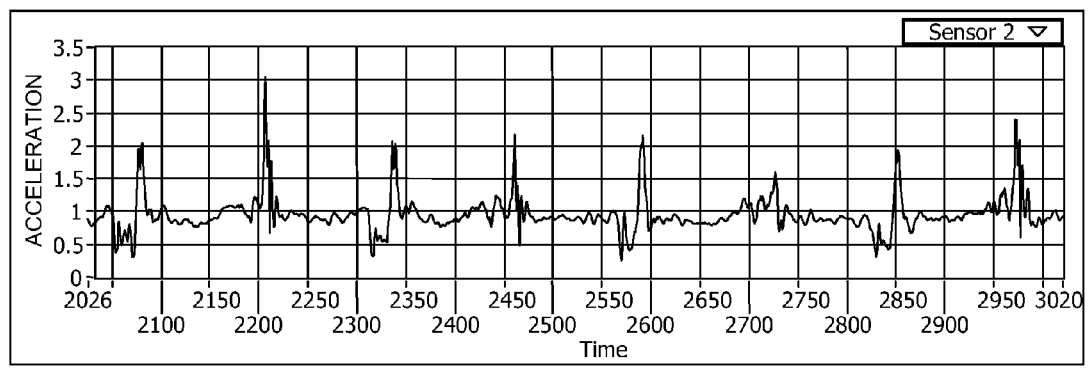

FIG. 10 is an exemplary set of biokinetographs illustrating dorsal spinal column disease showing foot slapping (high peaked amplitudes).

Figure 11:
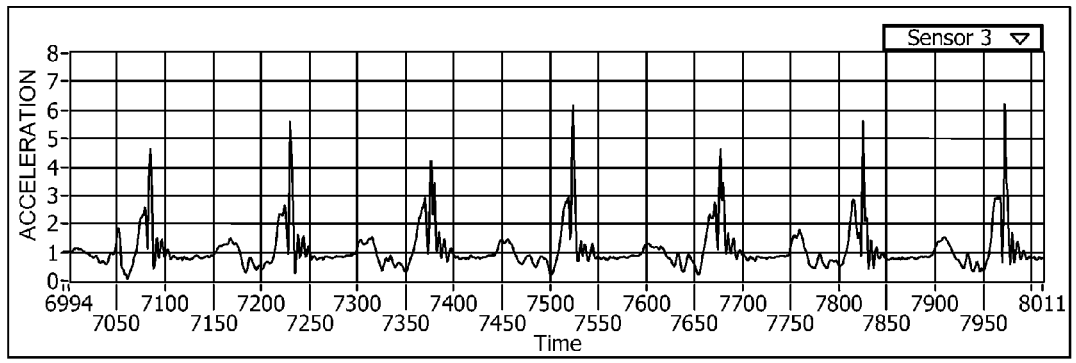
FIG. 11 is an exemplary set of biokinetographs 11000.
Figure 11:
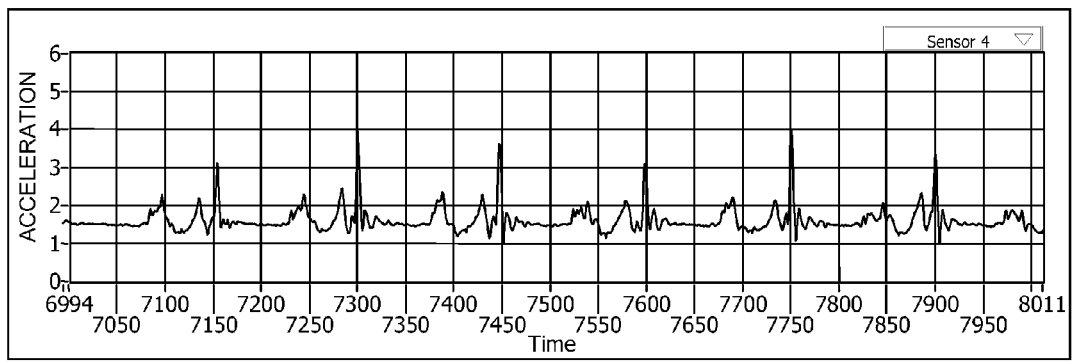
Figure 11:
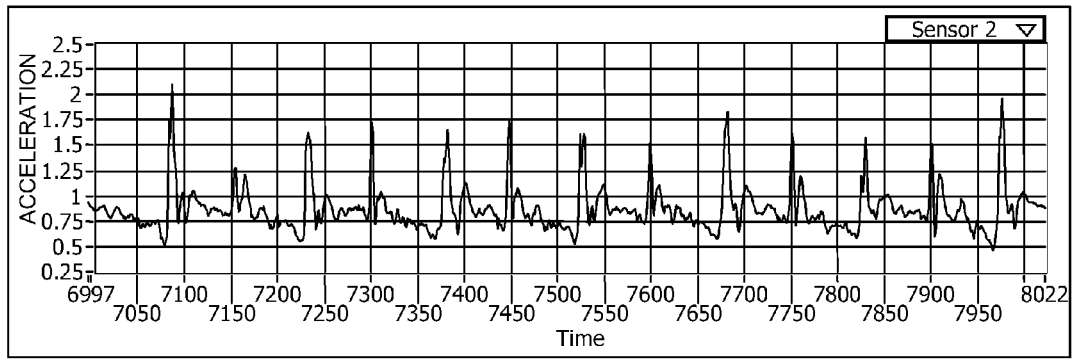

FIG. 11 is an exemplary set of biokinetographs illustrating right peroneal nerve injury (foot drop) showing abrupt toe off and premature toe strike. Note asymmetry of left and right amplitudes.

Figure 12:
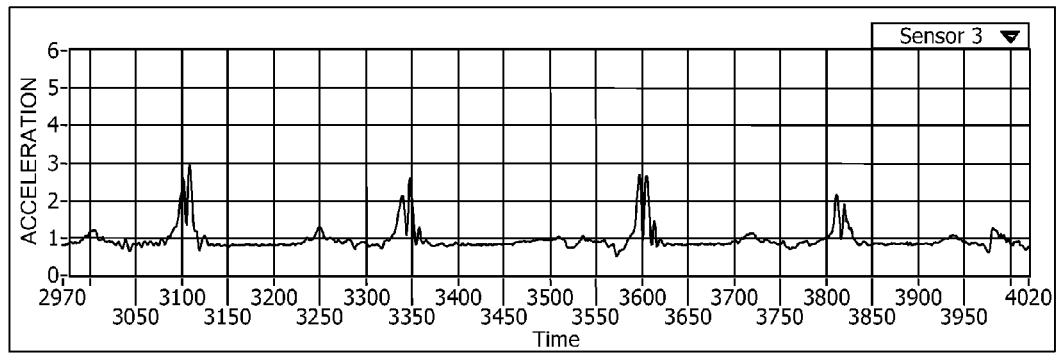
FIG. 12 is an exemplary set of biokinetographs 12000.
Figure 12:
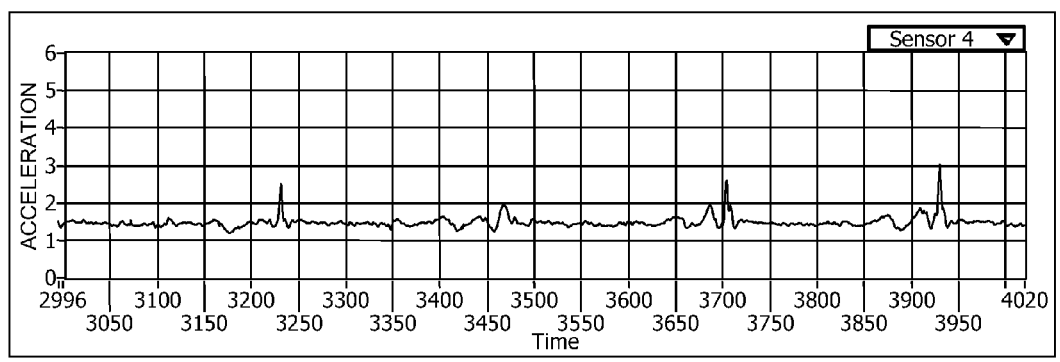
Figure 12:
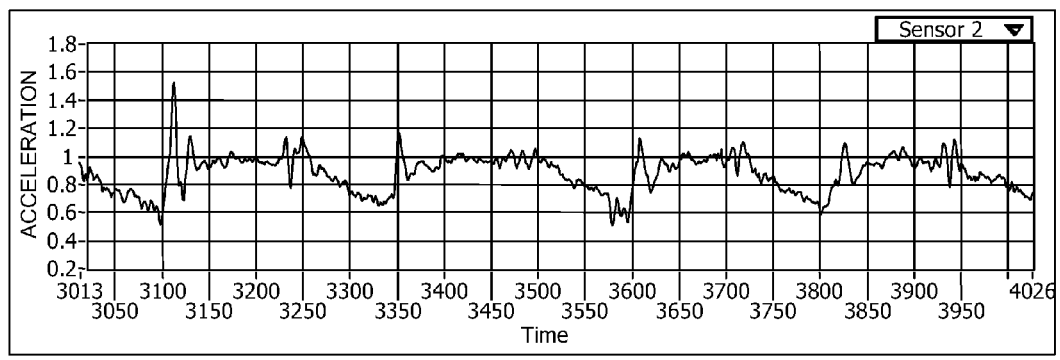
Figure 13:
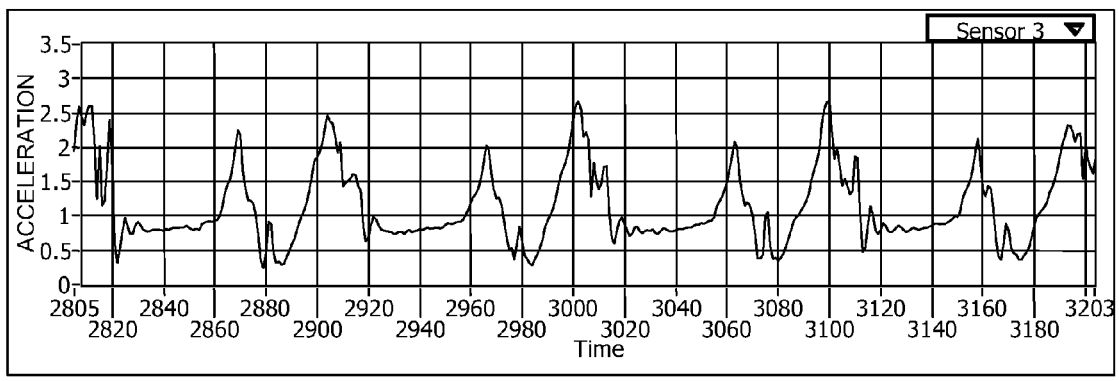
FIG. 13 is an exemplary set of biokinetographs 13000.
Figure 13:
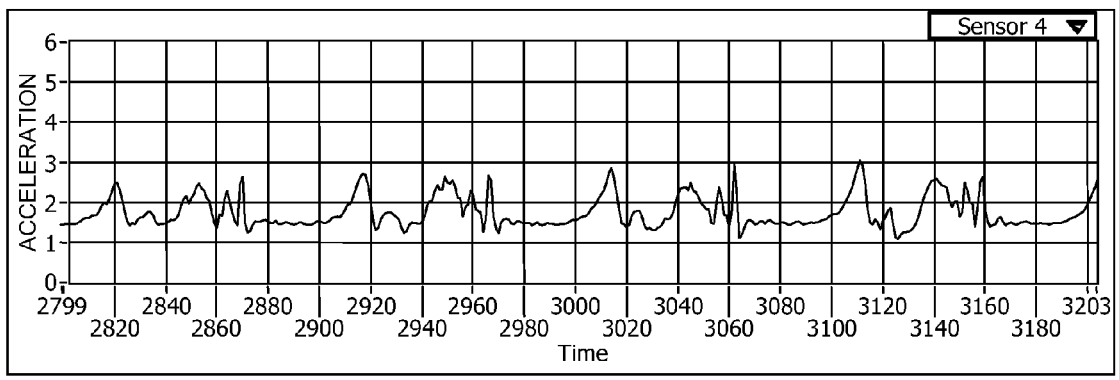
Figure 13:
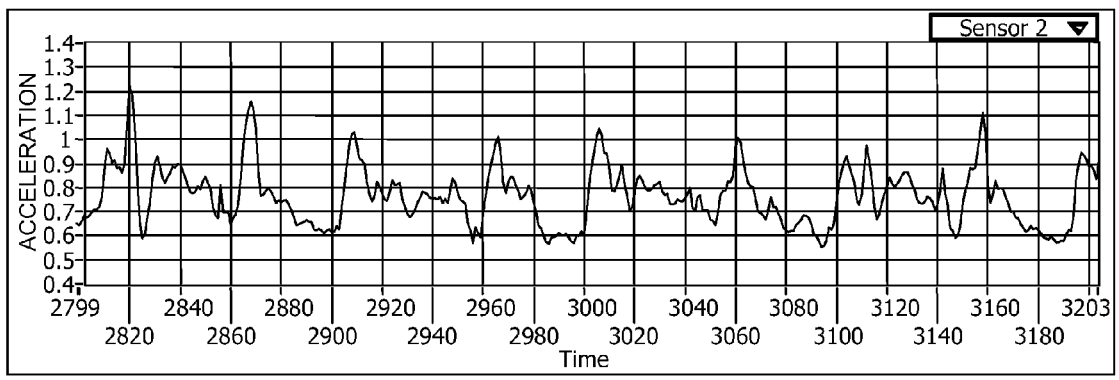

FIG. 12 is an exemplary set of biokinetographs illustrating left spastic hemiparesis showing gait asymmetry and pelvic rocking FIG. 13 is an exemplary set of biokinetographs providing a baseline for a 77 year old woman with painful right foot.

Figure 14:
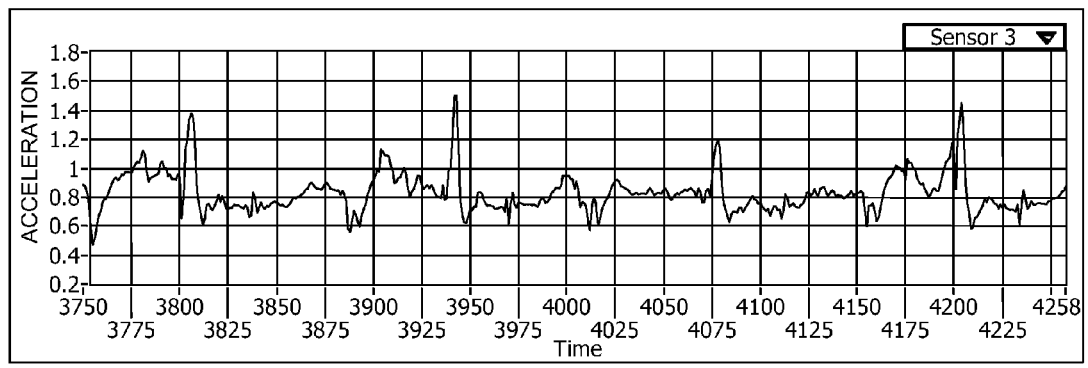
FIG. 14 is an exemplary set of biokinetographs 14000.
Figure 14:
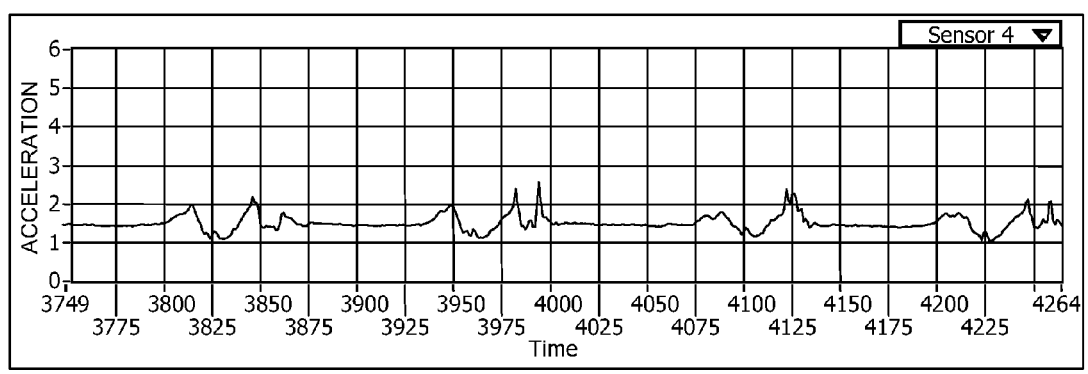
Figure 14:
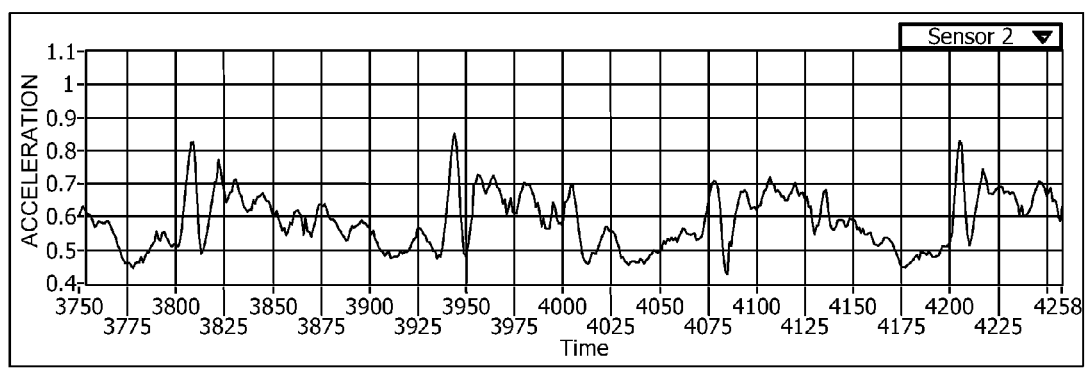

FIG. 14 is an exemplary set of biokinetographs for, one month later, the same woman with acute knee sprain.

Figure 15:
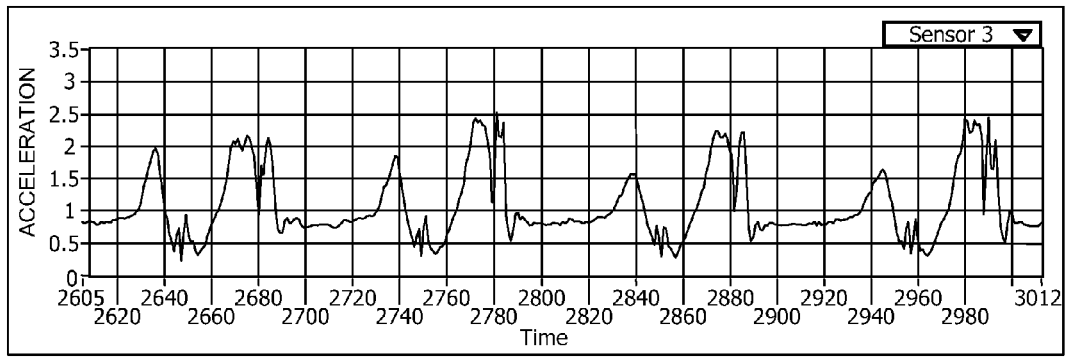
FIG. 15 is an exemplary set of biokinetographs 15000.
Figure 15:
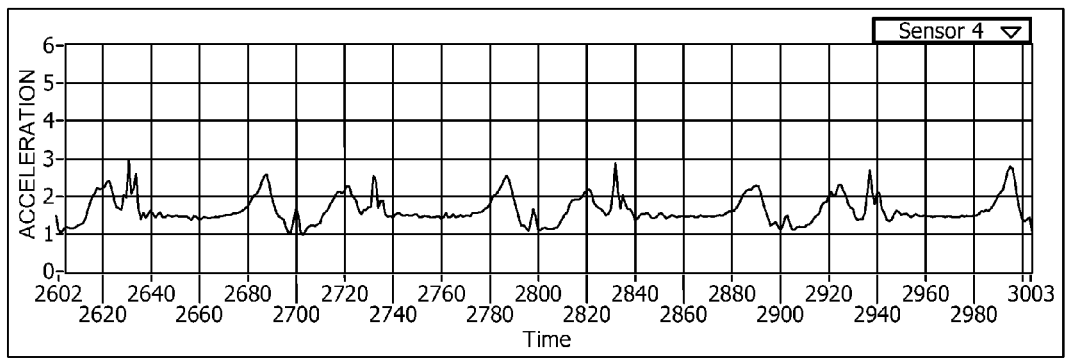
Figure 15:
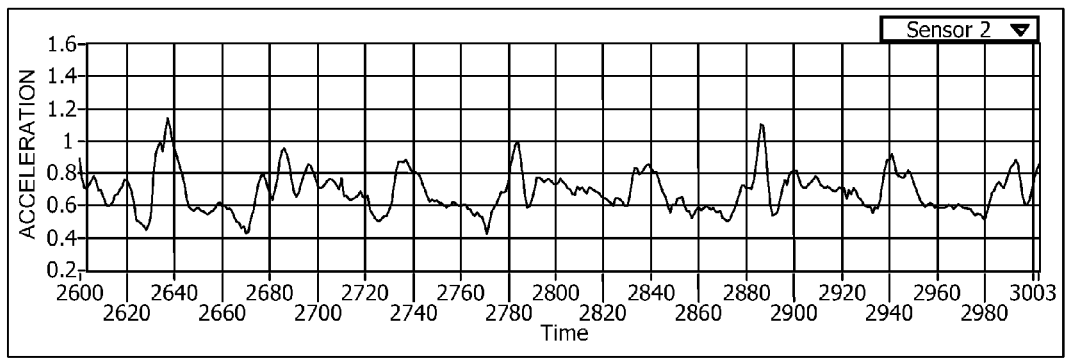

FIG. 15 is an exemplary set of biokinetographs for same woman one week after a knee sprain.

Figure 16:
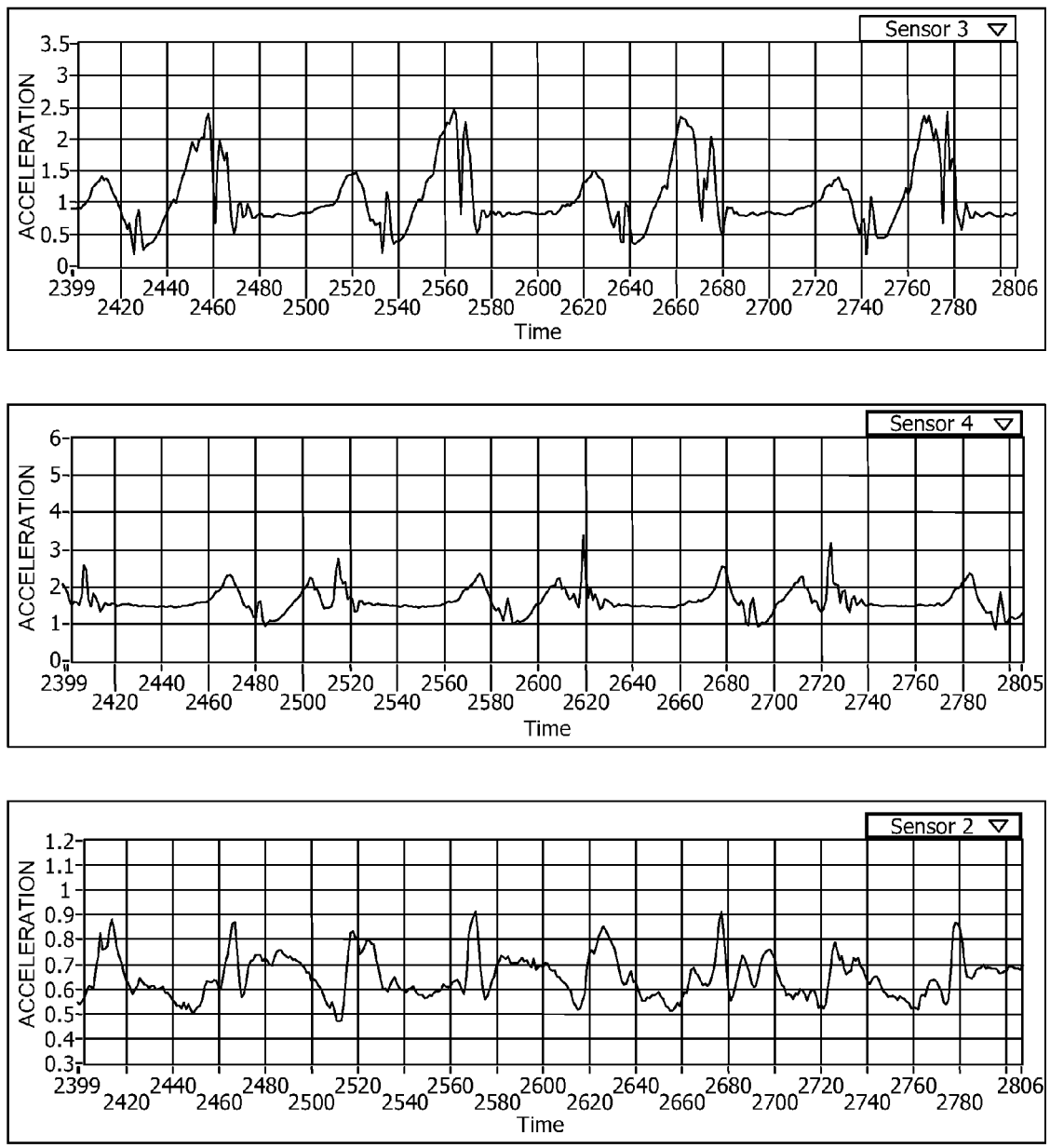
FIG. 16 is an exemplary set of biokinetographs 16000.

FIG. 16 is an exemplary set of biokinetographs for the same woman 2 weeks after the knee sprain.

Figure 17:
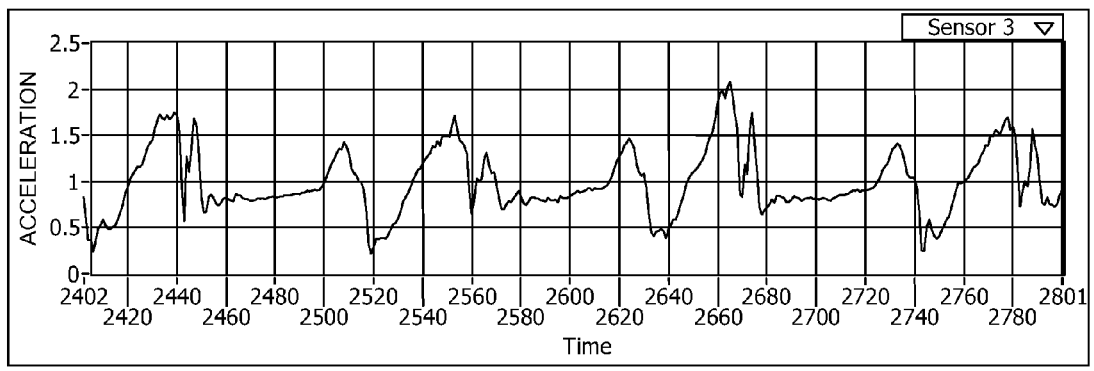
FIG. 17 is an exemplary set of biokinetographs 17000.
Figure 17:
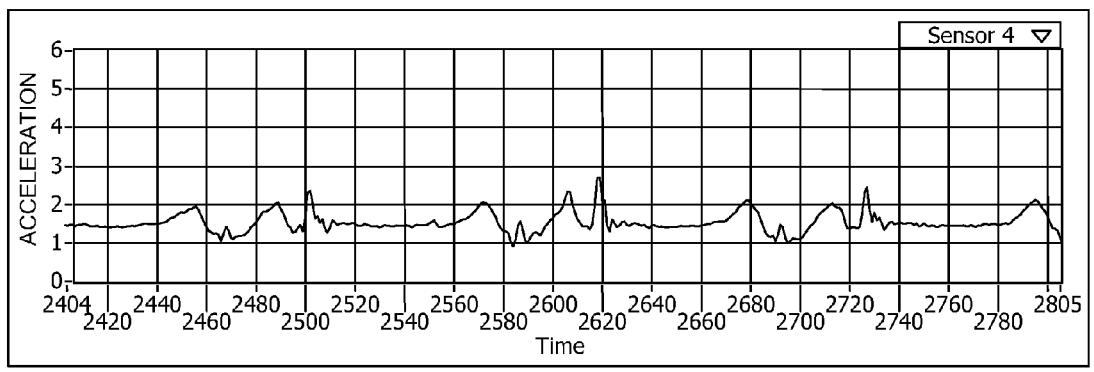
Figure 17:
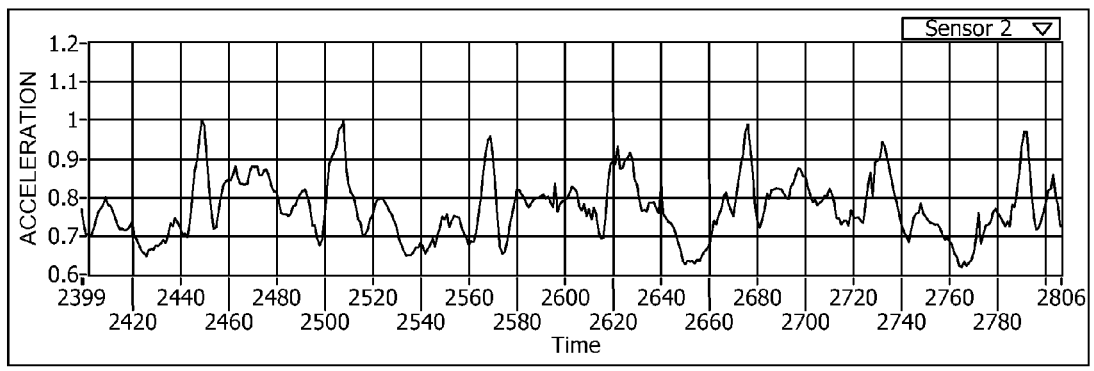

FIG. 17 is an exemplary set of biokinetographs for the same woman 3 weeks after the knee sprain.

Figure 18:
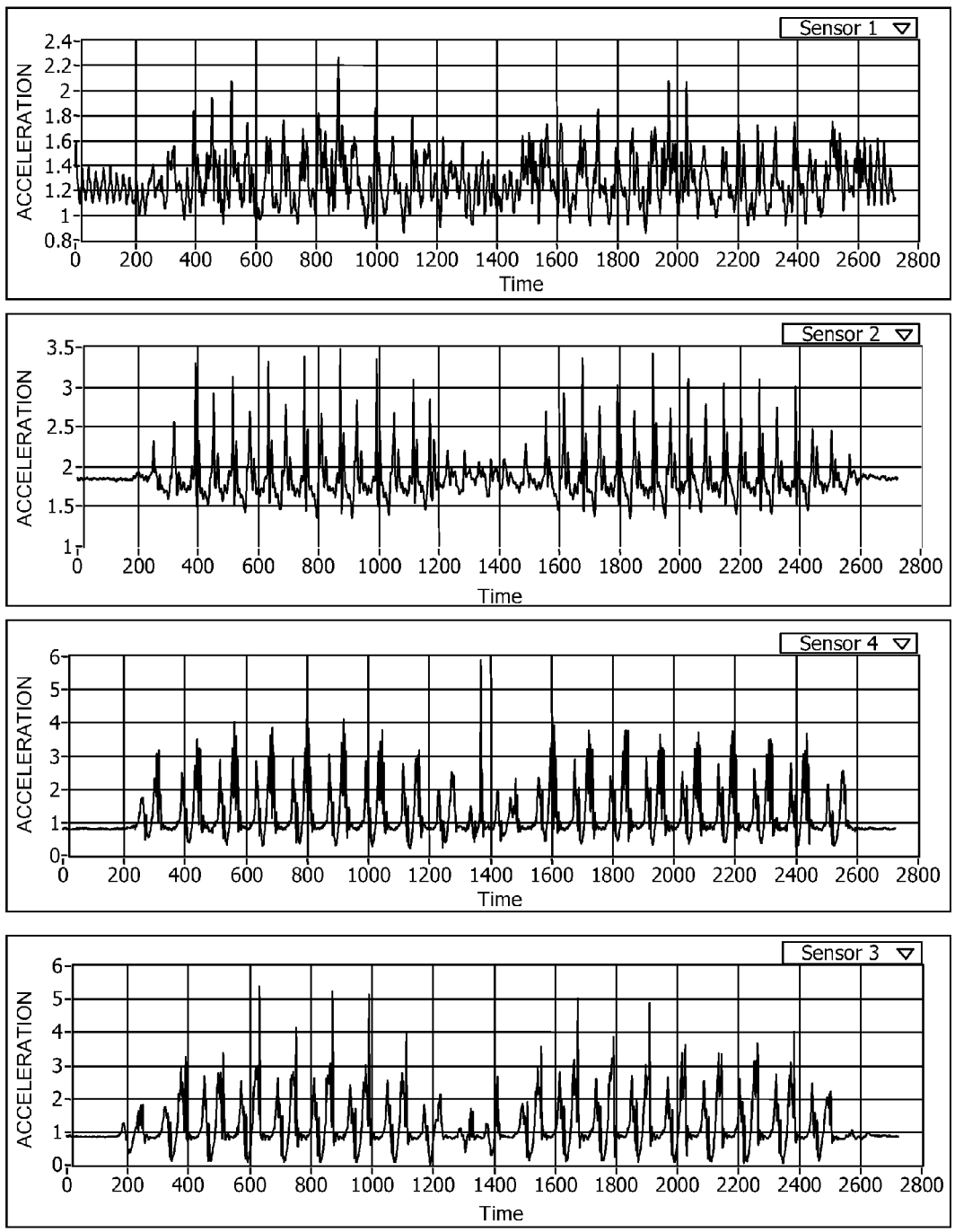
FIG. 18 is an exemplary set of biokinetographs 18000.

FIG. 18 is an exemplary set of biokinetographs illustrating Parkinson's disease showing resting arm tremor and delayed gait initiation.

Figure 19:
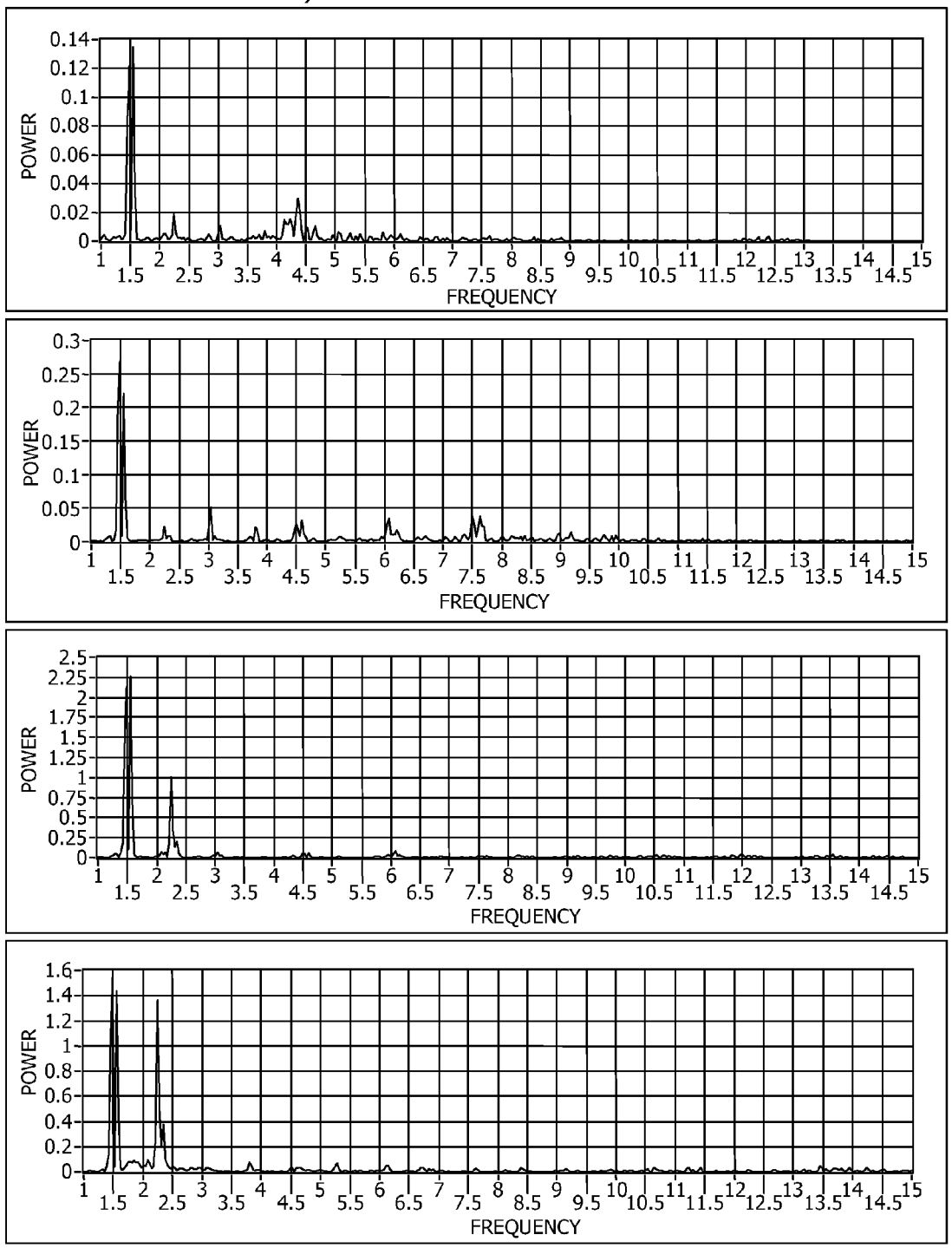
FIG. 19 is an exemplary set of biokinetographs 19000.

FIG. 19 is an exemplary set of biokinetographs illustrating FFTs for Parkinson's disease patient noted above (Note primary peak <1.8 Hz).

Figure 20:
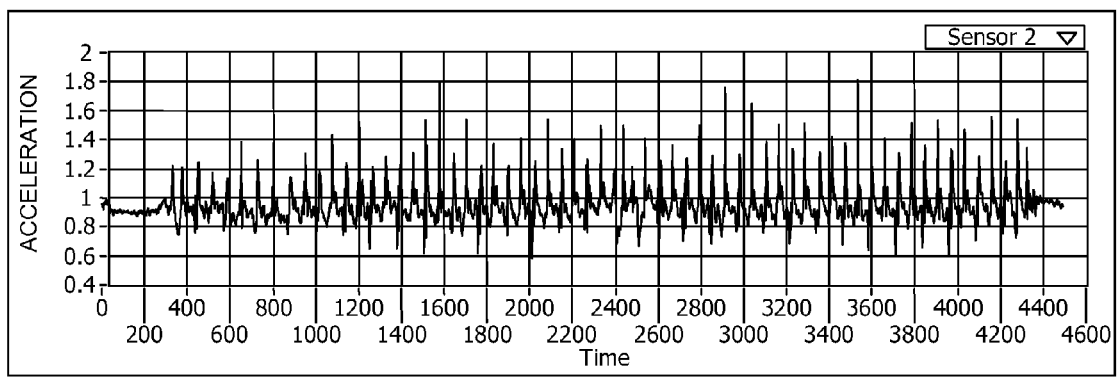
FIG. 20 is an exemplary set of biokinetographs 20000.
Figure 20:
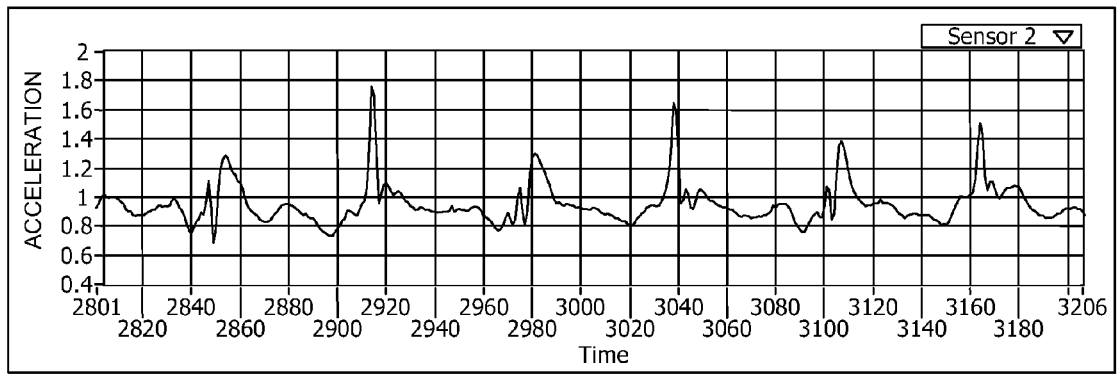

FIG. 20 is an exemplary set of biokinetographs illustrating sacral tracing of a patient with severe peripheral neuropathy showing exaggerated pelvic tilt with >0.2 g variation between steps.

Figure 21:
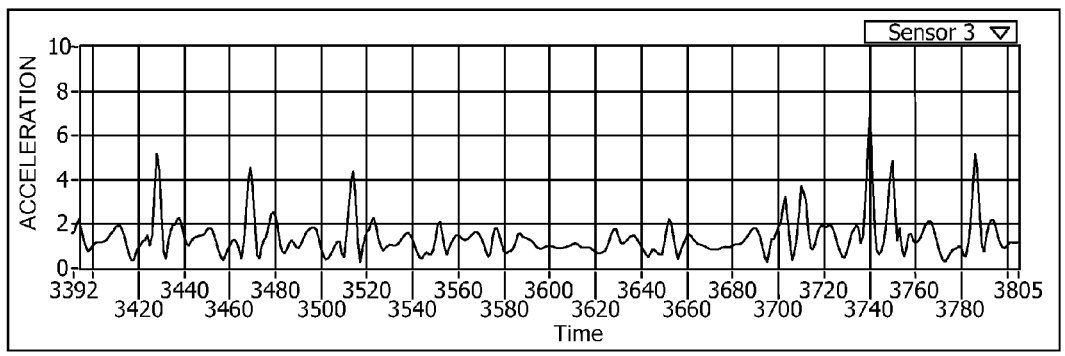
FIG. 21 is an exemplary set of biokinetographs 21000.
Figure 21:
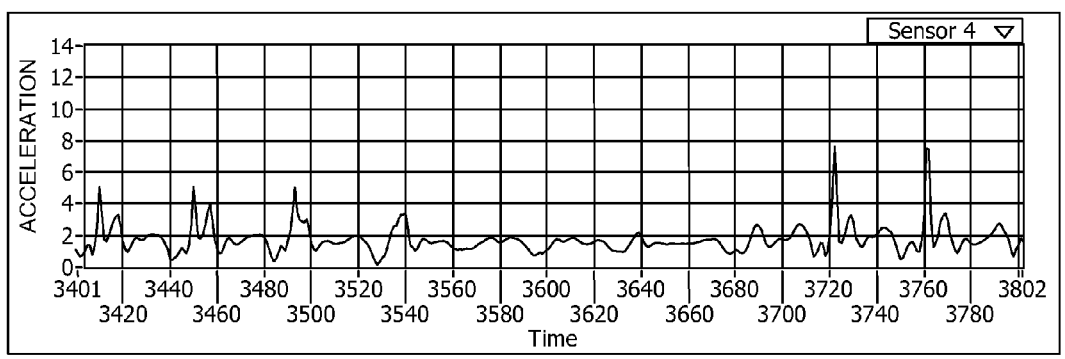
Figure 21:
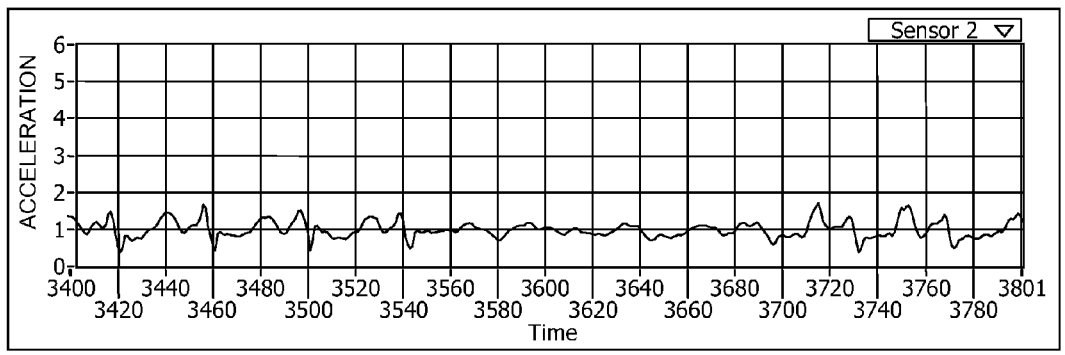

FIG. 21 is an exemplary set of biokinetographs illustrating Parkinson's turn around (greater than 5 small steps).

Figure 22:
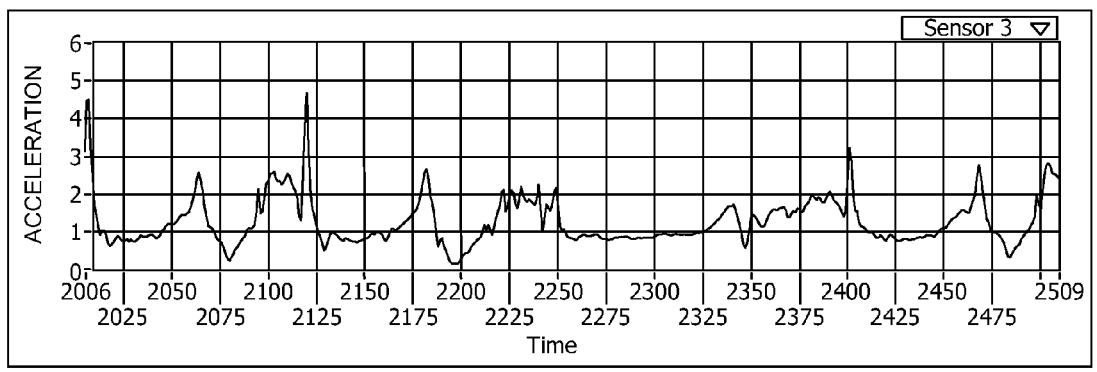
FIG. 22 is an exemplary set of biokinetographs 22000.
Figure 22:
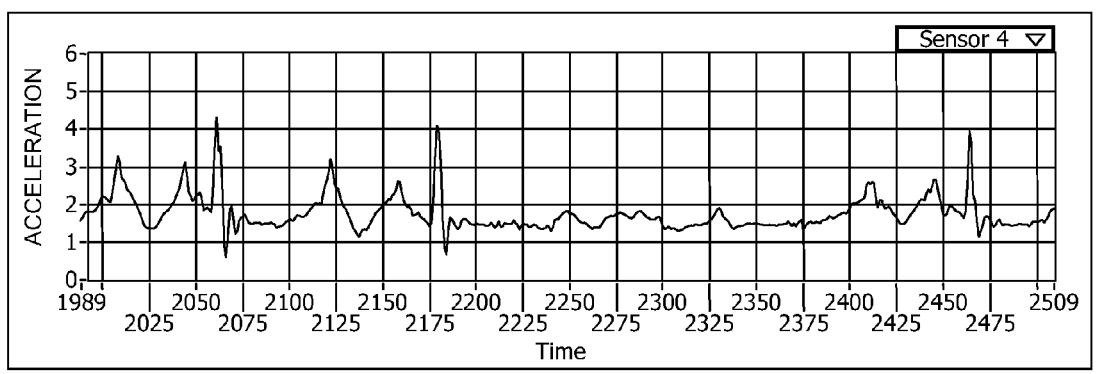
Figure 22:
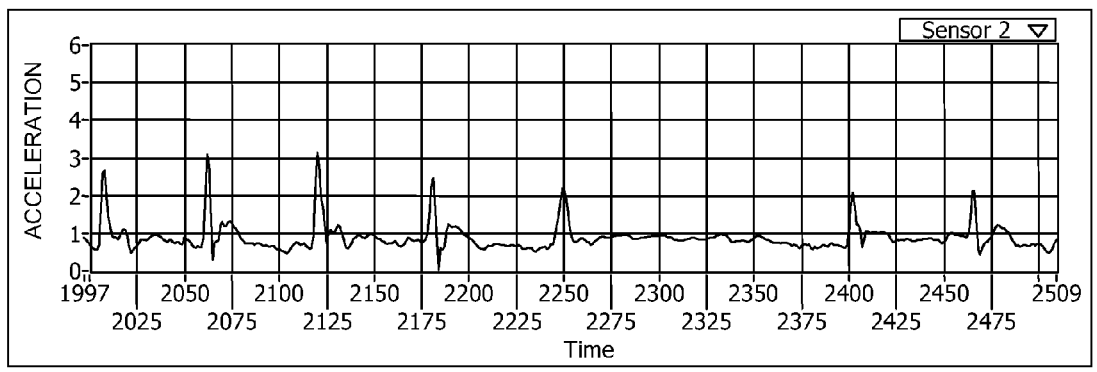

FIG. 22 is an exemplary set of biokinetographs illustrating normal turn around.

Figure 23:
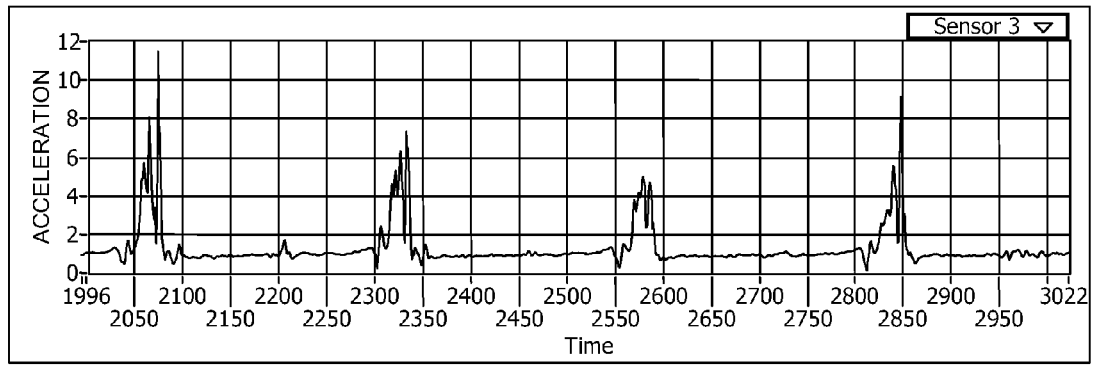
FIG. 23 is an exemplary set of biokinetographs 23000.
Figure 23:
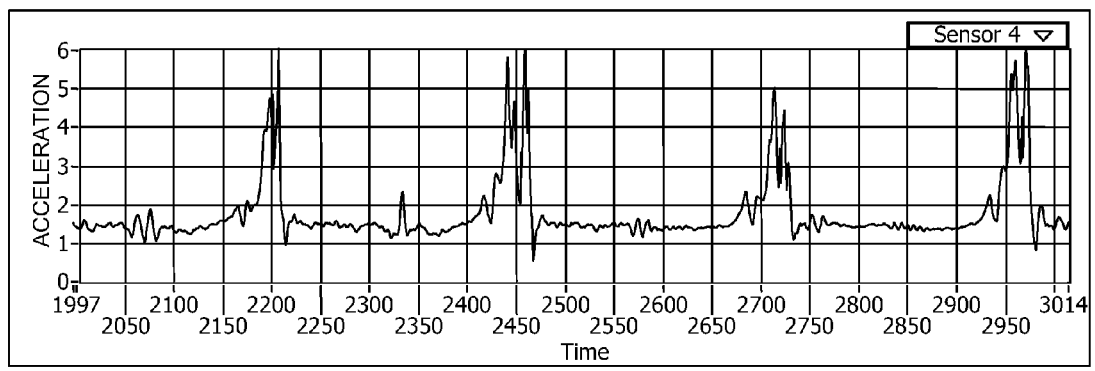
Figure 23:
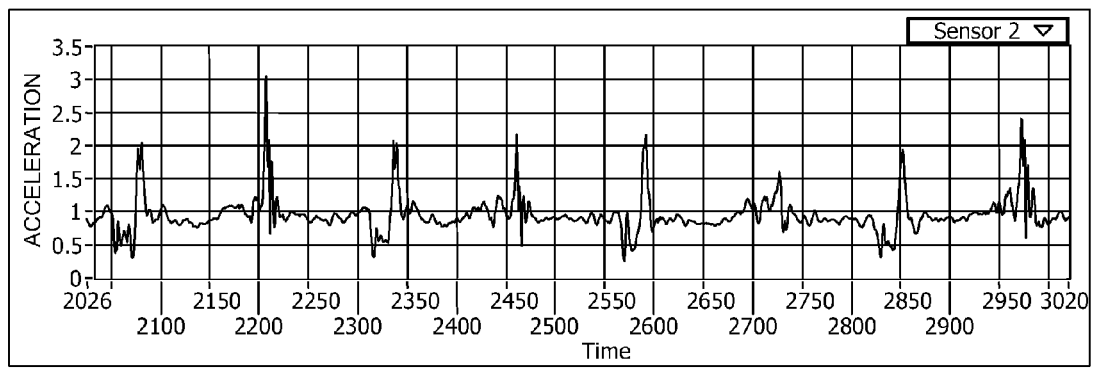
Figure 24A:
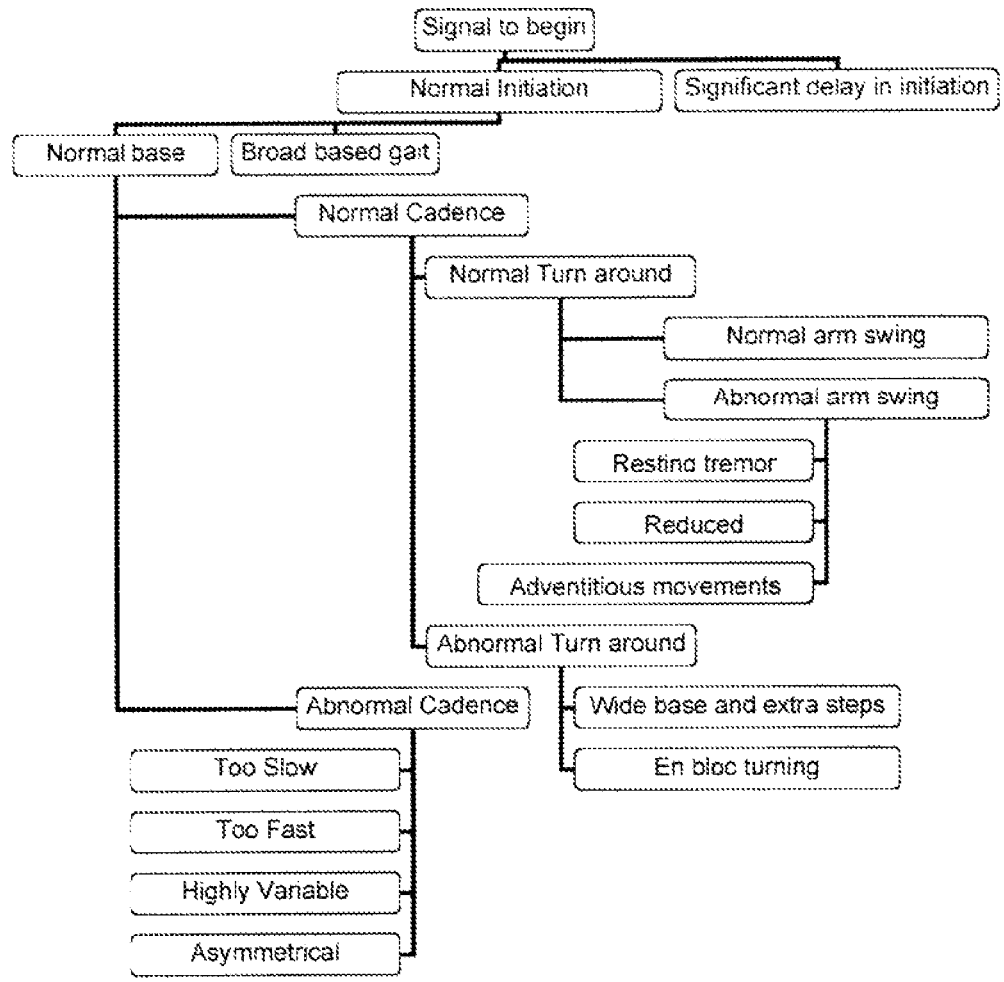
FIG. 24*a-g* is a flowchart of an exemplary embodiment of a method 24000.
Figure 24B:
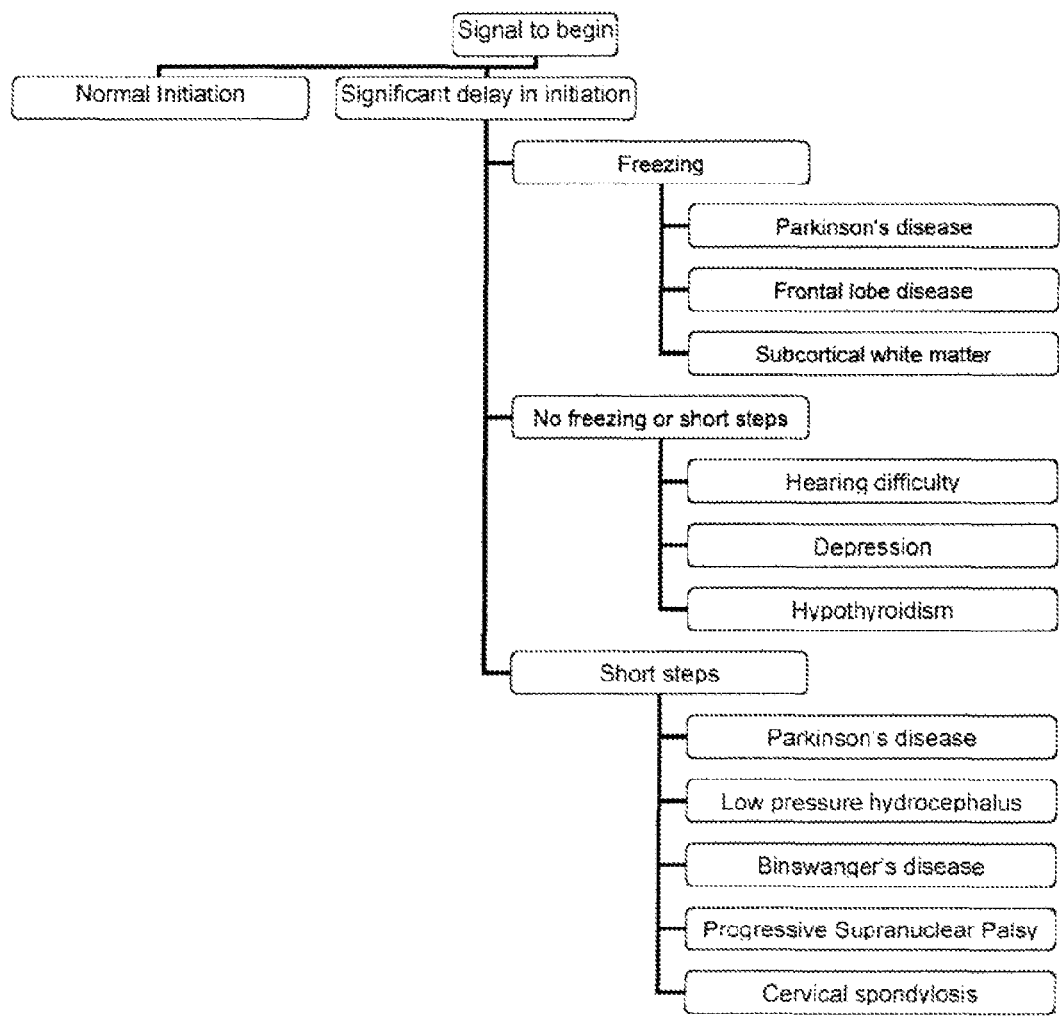
Figure 24C:
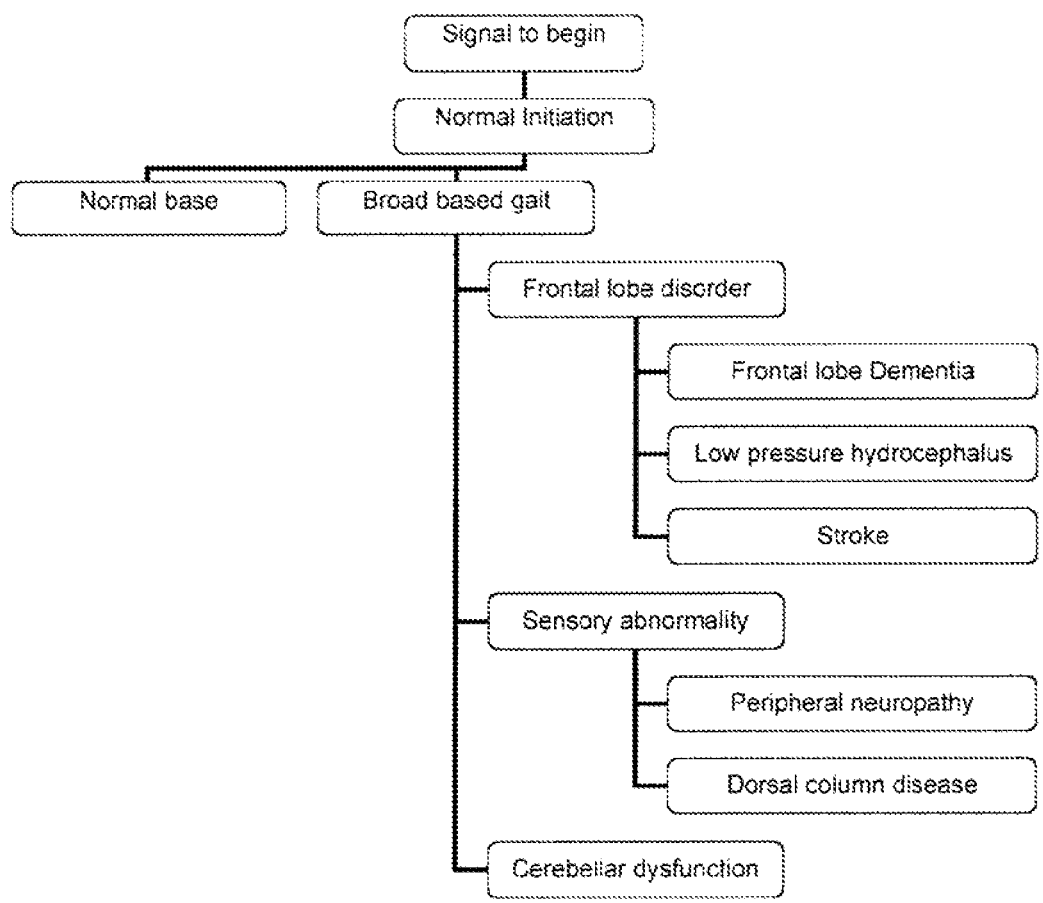
Figure 24D:
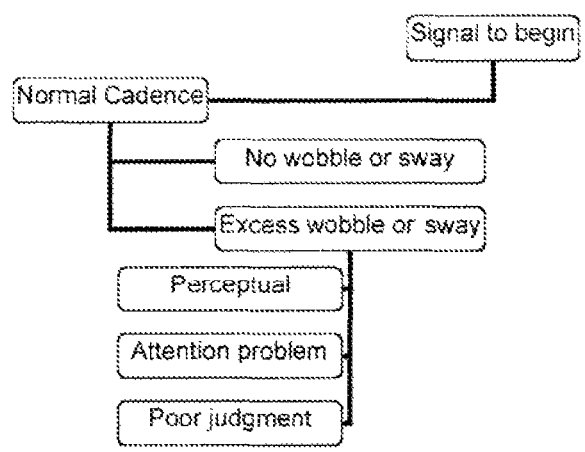
Figure 24E:
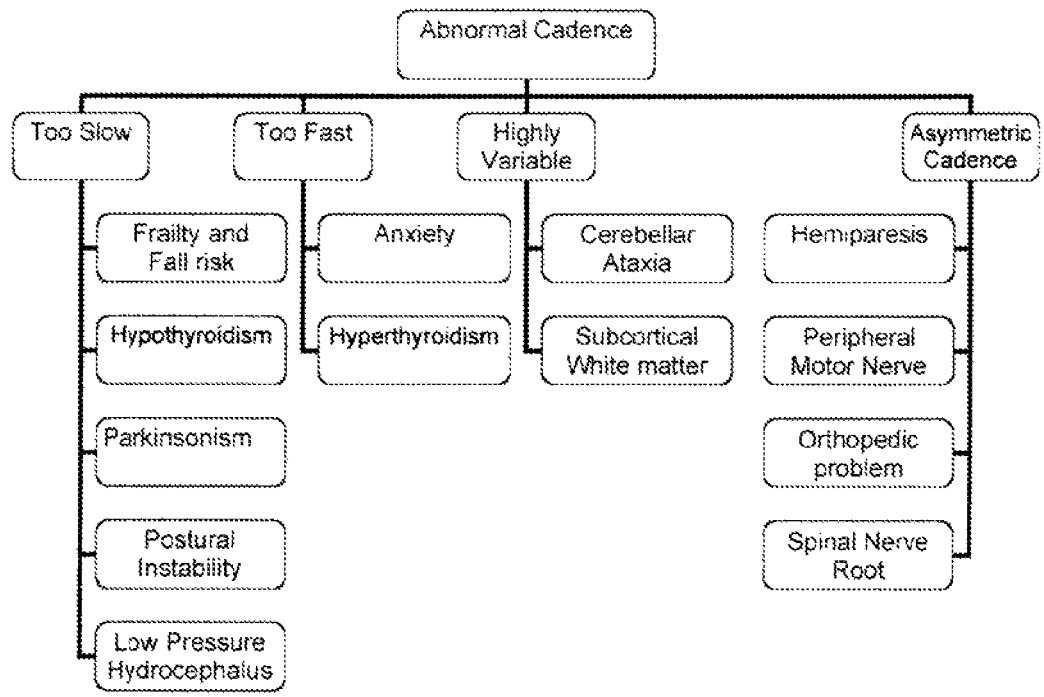
Figure 24F:
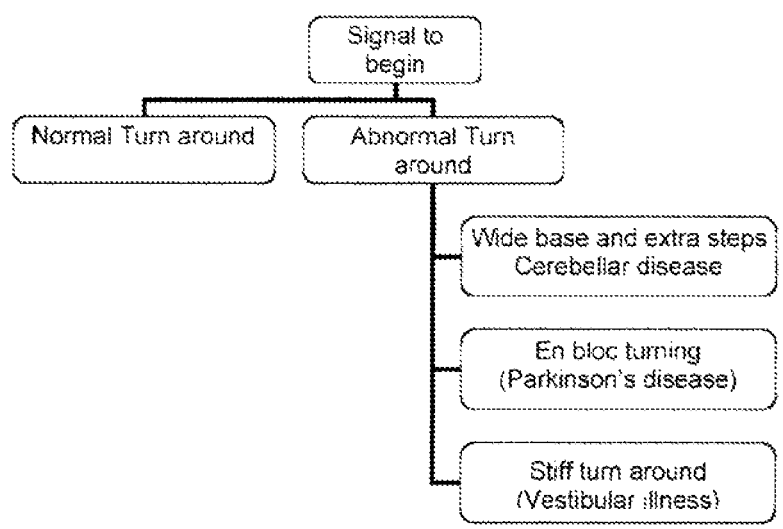
Figure 24G:
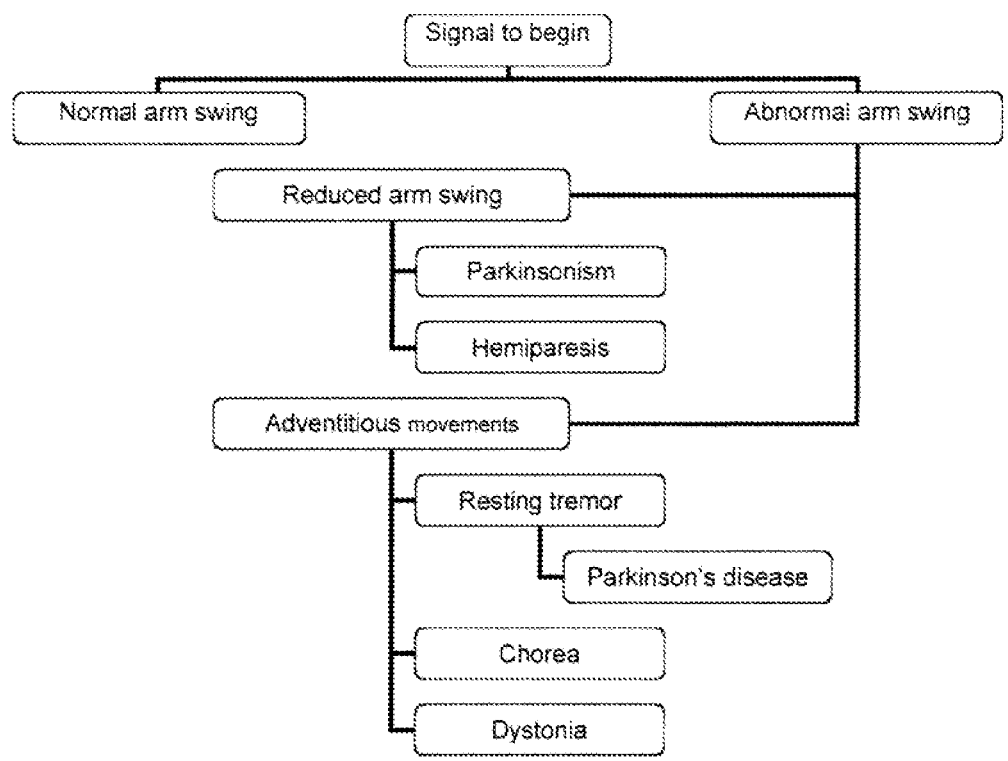

FIG. 23 is an exemplary set of biokinetographs illustrating cerebellar turn around (greater than 5 small steps with variability).

Basic Analytic Process

Certain exemplary embodiments can comprise a method that can comprise any of the following activities:

Obtaining the Biokinetographic Data

1. Informed consent to test the patient can be obtained.
2. The recording device can be attached to the waist with an elastic band and/or placed in a position just behind the left hip (so that it does not impede the left arm swing).
3. The biokinetographic sensors can be individually attached to the small of the back near the sacrum (tucked under the elastic band), right wrist, and/or just above each ankle (by Velcro straps) on the outside of the lower leg. The sensors can be placed so that they are very close to being parallel or perpendicular to the axis of movement. For the ankles and wrists, the x vector can represent forward-backward (i.e. in the direction of forward motion), the y vector can be vertical, and the z vector can be side-to-side (perpendicular to x in the horizontal plane). For the sacrum, the x and z vectors can be transposed (x being side-to-side, and z being forward and backward) since the sensor can be placed flat against the patient's back. This can rotate the sensor 90 degrees in the horizontal plane compared to the ankle and/or wrist sensors (the ankle sensors can be placed just above the outside ankle prominence, lateral malleolus in medical parlance). Other sensors can be placed on other body locations. The sensor wires can attach directly to the recorder by standard electrical connectors and/or any dangling excess in wire length can be tucked under the waist band near the recorder (to avoid tripping). Each sensor can record at a rate of 120 Hz on a dedicated channel and/or all the data (4 channels) can be stored in the recorder on, for example, a memory chip, such as an 8 MB digital flash and/or EEPROM memory chip (such as used by digital cameras).

4. The patient can walk to the starting point at the end of a straight 45 foot hall.

5. The recorder can be turned on to begin simultaneous recording on all 4 channels.

6. The patient can walk, e.g., down a hall, at their normal walking pace, turn around, and/or walk back to the starting point. There need be no preliminary trial, however, if the patient is interrupted by another person or if a sensor wire dislodges, the trial can be aborted and restarted from the beginning 7. The recorder can be turned off and/or the device can be detached from the patient.

8. The memory chip can be removed from the recorder and/or placed in a plastic labeled protector for transportation.

9. The information from the memory chip can be downloaded into a software program and/or stored in a computer file.

Analyzing the Biokinetographic Data

1. The raw computer file can be loaded into a software program and/or each channel initially can be displayed as the simple linear sum of the x, y, and z vectors at each site over time or various combinations of sums (such as xz or zy) to produce a biokinetographic signature. Up to four or more channels can be visualized on a single screen. The software can allow each vector (x, y, or z) to be graphed individually and/or in various combinations. The software can display the power spectra (Fast Fourier Transformation) for each channel. In certain exemplary embodiments, channel one can be the right arm sensor, channel two can be the sacrum sensor, channel three can be the right lower leg sensor, and/or channel four can be the left lower leg sensor.

2. The 4 channel biokinetic tracing can be examined for 1) symmetry of the movement clusters, 2) any obvious rhythms in the patterns, 3) the nature of the "turn around" pattern and/or gait initiation, and/or 4) artifacts and/or grossly abnormal values. The power spectra can be inspected for magnitude and frequency of the peaks.

Note: useful diagnostic information can be available from this initial inspection. For example:

1) A delay in initiating movement can increase the likelihood of Parkinson's disease;

2) Reduced global arm swing can increase the possibility of Parkinson's disease;

3) A low frequency resting tremor seen at the beginning of the tracing can significantly increase the likelihood of Parkinson's disease;

4) An "en bloc" turning pattern can significantly increase the possibility of Parkinson's disease;

5) Excess wobble or sway on turning can suggest a neurological problem such as Parkinson's disease, cerebellar disease, dorsal spinal column disease, low pressure hydrocephalus, and/or peripheral neuropathy;

6) Reduced amplitudes (one g or less) of the leg waveforms can increase the likelihood of frailty and/or fall risk;

7) Power spectra with very low, multiple peaks can increase the likelihood of frailty and/or fall risk; and/or 8) Power spectra with initial frequencies less than 1.8 Hz can increase the likelihood of frailty and/or fall risk.

3. A representative 3 second time frame can be visually selected for more detailed analysis beginning 3 waves after the turn around (assuming no obvious artifact is evident; if so, then 3 waves after the artifact is used) and/or a printout of the biokinetograph can be obtained.

4. The 3 second left and right ankle biokinetic tracing can be used to obtain timing intervals for the various components of the waveform that relate directly to the gait cycle. The labeling of the biokinetic tracing is shown in FIGS. 1, 2, and 3. The specific intervals and/or their method of calculation can be:

1) The heel strike interval can be the interval from heel strike to heel strike;

2) Single stance time can be the interval from heel strike to toe off;

3) Heel to toe interval can be the time from heel strike to toe strike;

4) Swing through can be the interval from toe off to heel strike (note that swing through plus single stance time equals heel strike interval);

5) Initial swing can be the interval from toe off to little peak in early swing through;

6) Double stance one can be the interval from heel strike to opposite leg toe off, just prior to opposite swing through; and/or 7) Double stance two can be the interval from opposite leg heel strike to toe off, just prior to swing through.

5. The 3 second left and right ankle biokinetic tracing can be used to obtain acceleration amplitudes for the heel strike, toe strike, toe off, and/or initial swing peaks. These can be calculated as the height of the peak minus one gravitational unit (g). One g can be considered the acceleration when the foot is stationary on the ground and experiencing only the force of gravity.

6. The power (height) and frequency of the first and second spectral waves can be noted for the arm, sacral, and/or left and right ankle tracings.

7. Timing intervals, acceleration amplitudes, and/or spectral power and frequency can be entered into a customized spreadsheet to calculate specific aspects of the gait cycle. These calculations can include:

1) Cadence, which can be steps per minute, can be calculated by dividing 60 by the average of the left and right heel strike intervals (in seconds).

2) The percentage of time spent in single stance phase for the left and right legs can be calculated by single stance time divided by the heel strike interval.

3) The percentage of time in swing phase for the left and right legs can be calculated by the swing through divided by the heel strike interval. As a mathematical check, the percentages of the stance phase and swing phase should add to 100%.

4) The percentage of time in foot strike can be calculated by dividing the heel to toe strike interval by the heel strike interval.

5) The percentage of time spent in double stance phase can be calculated by dividing the sum of double strike phase one and double strike phase two by the heel strike interval.

6) Double strike delta can be the absolute difference between double strike one and double strike two.

7) Heel strike delta can be the absolute difference between the left and right heel strike acceleration amplitudes.

8) Toe strike delta can be the absolute difference between the left and right toe strike acceleration amplitudes.

9) Toe off delta can be the absolute difference between the left and right toe off acceleration amplitudes.

10) Initial swing delta can be the absolute difference between the left and right initial swing acceleration amplitudes.

11) Single stance total can be the sum of the left and right single stance times.

12) Heel to toe total can be the sum of the left and right heel to toe times.

13) Initial swing total can be the sum of the left and right initial swing times.

14) Swing through total can be the sum of the left and right swing through times.

15) Double stance total can be the sum of the first and second double stance times.

16) Heel strike total can be the sum of the left and right heel strike amplitudes.

17) Toe strike total can be the sum of the left and right toe strike amplitudes.

18) Toe off total can be the sum of the left and right toe off amplitudes.

19) Initial swing total can be the sum of the left and right initial swing amplitudes.

20) Total g can be the sum of the heel strike total, toe strike total, toe off total and initial swing total.

8. Analysis of a single vector. Analysis of each vector and/or the relationships between vectors and the vector sum can be very useful. For example, when walking straight ahead, the z vector at the ankle and/or the x vector at the sacrum (both of which can measure side-to-side motion) can be markers of "wobble", "sway", and/or "degree of staggering", which, if pronounced, can imply navigational difficulty. The vertical (y) vector can be used to determine the degree of foot shuffling and/or rate of heel rise, which can be a useful clue at the sacrum (center of mass) in determining step symmetry (equal rise with each step). These are just a few possible examples.

In certain exemplary embodiments, analysis of biokinetographic data can help identify specific biokinetographic patterns, such as those suggestive of Parkinson's disease, hemiparesis, cerebellar disease, frontal lobe disease, low pressure hydrocephalus, spinal stenosis, orthopedic conditions (pain, arthritis, injury, etc.), motor neuropathy, myopathy, and/or others.

Certain exemplary embodiments can comprise a system and/or method for the diagnosis of critical conditions and/or for the diagnosis of the advanced onset of critical conditions, which can comprise: a sensing means (e.g., a plurality of sensors removably affixed to a patient and/or otherwise oriented so as to measure accelerations, positions, and/or related variables involving certain parts of the body); a recording means; and/or an analysis means (comprised of, e.g., a graphical interface, a data processor, a storage database, and/or a display means).

Certain exemplary embodiments can comprise a method and/or system for the diagnosis of critical conditions and/or for the diagnosis of the advanced onset of critical conditions, which can comprise: removably affixing a plurality of sensors to a patient; sensing and recording data related to the motion of parts of the body (e.g., translational motion, rotational motion, velocity, acceleration, position, etc., hereafter, gait measurement data) of the patient over time as the patient performs some sort of physical activity such as walking; and/or analyzing gait measurement data in comparison to normal (healthy) baselines and/or in comparison to prior measurement data previously taken from the patient.

Table 2 provides exemplary diagnostic biokinetographic features and their potential criteria.

TABLE 2

| Movement feature | Biokinetographic Criteria | Clinical Implication | Comments |
|---|---|---|---|
| A. Delayed initiation of movement | Greater than 1.5 seconds after start signal | Integrity of sensory and locomotor coordination | |
| 1. Delayed initiation with freezing or short steps | Freezing is >2.0 second delay<br>Short steps = FFT frequency <1.8 | Parkinson's disease<br>Frontal lobe disease<br>Low pressure hydrocephalus<br>Subcortical white matter disease | Step length tends to normalize after several steps in Frontal lobe disease and low pressure hydrocephalus |
| 2. Delayed initiation with no freezing or short steps | FFT frequency ≥1.8 | Hearing impairment<br>Depression<br>Hypothyroidism | |
| B. Broad based gait | Exaggerated pelvic tilt<br>>0.15 g variation between steps at the sacral sensor | Frontal lobe, sensory (dorsal spinal column disease or peripheral neuropathy) or cerebellar dysfunction | |
| C. Abnormal cadence | Normal is between 100 and 120 steps per minute | Cadence implies overall motor coordination | Normal steps are regular and symmetrical |
| 1. Too fast | >120 steps per minute<br>Heel strike interval less than 250 milliseconds | Hyperthyroidism<br>Anxiety<br>Competitive personality | The higher the number the more abnormal the cadence |
| 2. Too slow | <100 steps per minute<br>Heel strike interval greater than 330 milliseconds | Hypothyroidism<br>Parkinsonism<br>Postural instability<br>Low pressure hydrocephalus | Slow cadence denotes frailty and increased risk of falling |
| 3. Highly variable | >1 g difference in heel strike amplitudes or FFT power <0.5 | Cerebellar ataxia<br>Subcortical white matter disease<br>Progressive supranuclear palsy | Also implies perceptual problem, attention problem or poor judgment |
| 4. Asymmetrical | Difference in double stance times greater than 25 milliseconds | Spastic hemiparesis<br>Peripheral nerve injury<br>Spinal nerve root (radiculopathy) | Orthopedic problems include hip, knee, ankle, foot or leg muscle, |

TABLE 2-continued

| Movement feature | Biokinetographic Criteria | Clinical Implication | Comments |
| --- | --- | --- | --- |
| | | Focal orthopedic concern (joint, bone, muscle or connective tissue) Amputation Vascular disease | tendon or bursa problems |
| D. Abnormal turn around | Five or more turn steps | Cerebellar disease Parkinsonism | Subtleties may appear here since it is more demanding than walking straight |
| E. Abnormal arm swing | | | |
| 1. Reduced | Arm sensor amplitude less than 0.5 g or FFT power <0.5 | Parkinsonism Hemiparesis (usually from a stroke) | |
| 2. Adventitious movements | Resting tremor seen on wrist sensor baseline | Parkinsonism | |
| | Wide fluctuations in wrist sensor | Chorea Dystonia | |

FIGS. 24a-g depict a flowchart of an exemplary embodiment of a method 24000, which can be useful for the diagnosis of critical conditions and/or for the diagnosis of the advanced onset of critical conditions, based on gait measurement data, biokinetographic data, biokinetographic features, and/or biokinetographic criteria.

Certain exemplary embodiments can comprise a method that comprises associating a plurality of biokinetographic comparison results with a first specific dysfunction from a group of specific dysfunctions, each of the biokinetographic comparison results obtained from a comparison of a biokinetographic value to a standard for a corresponding biokinetographic variable.

Figure 25:
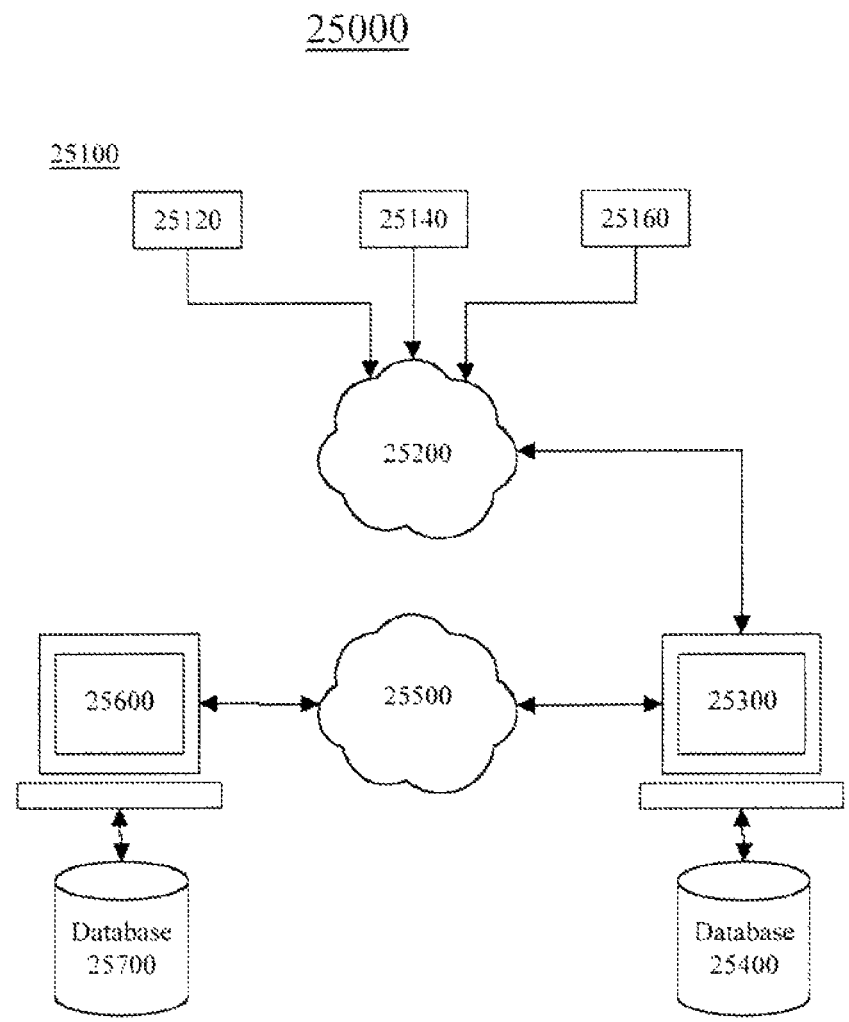
FIG. 25 is a block diagram of an exemplary embodiment of a system 25000.

FIG. 25 is a block diagram of an exemplary embodiment of a system 25000, which can comprise any number of sensors 25100, such as such as accelerometers, velocimeters, position sensors, strain gages, pressure sensors, etc., 25120, 25140, and 25160. Sensors 25100 can be coupled via a network 25200 to an biokinetographic information device 25300, which can, for example, receive, store, process, and/or transmit data, such a biokinetographic data. For example, based on biokinetographic criteria stored in communicatively coupled database 25400, information device 25300 can assess biokinetographic data and/or assist with diagnosing a condition. Via network 25500 (and/or network 25200), information can be shared between biokinetographic information device 25300 and other information devices, such as a healthcare records server 25600 to which a healthcare records repository and/or database 25700 is communicatively coupled.

Figure 26:
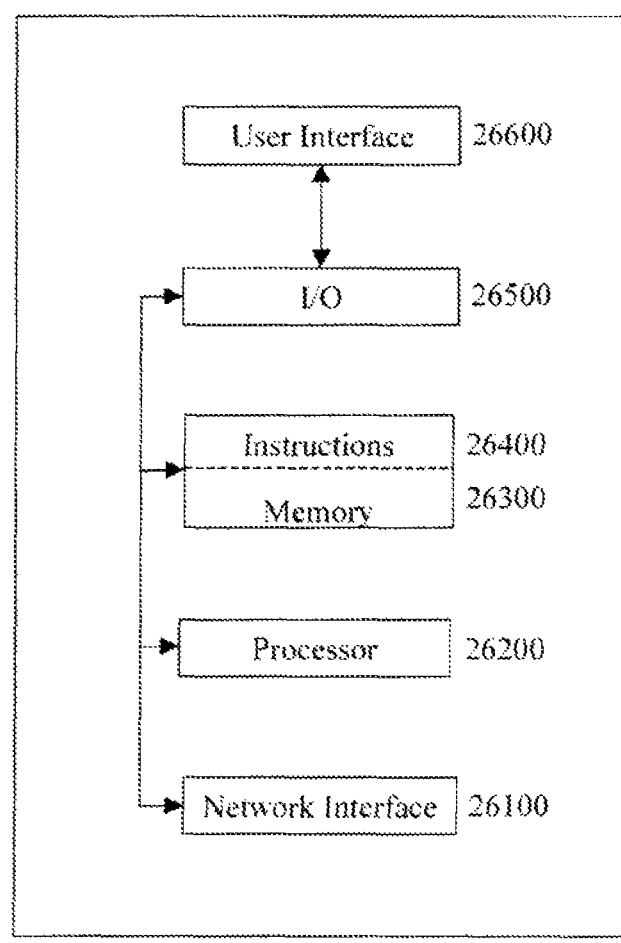
FIG. 26 is a flowchart of an exemplary embodiment of a method 26000.

FIG. 26 is a block diagram of an exemplary embodiment of an information device 26000, which in certain operative embodiments can comprise, for example, server 25600, information device 25300, etc. of FIG. 25. Information device 26000 can comprise any of numerous components, such as for example, one or more network interfaces 26100, one or more processors 26200, one or more memories 26300 containing machine instructions 26400, one or more input/output (I/O) devices 26500, and/or one or more user interfaces 26600 coupled to I/O device 26500, etc.

In certain exemplary embodiments, via one or more user interfaces 26600, such as a graphical user interface, a user can view a rendering of information related to researching, designing, modeling, creating, developing, building, manufacturing, operating, maintaining, storing, marketing, selling, delivering, selecting, specifying, requesting, ordering, receiving, returning, rating, and/or recommending any of the products, services, methods, and/or information described herein.

Figure 27:
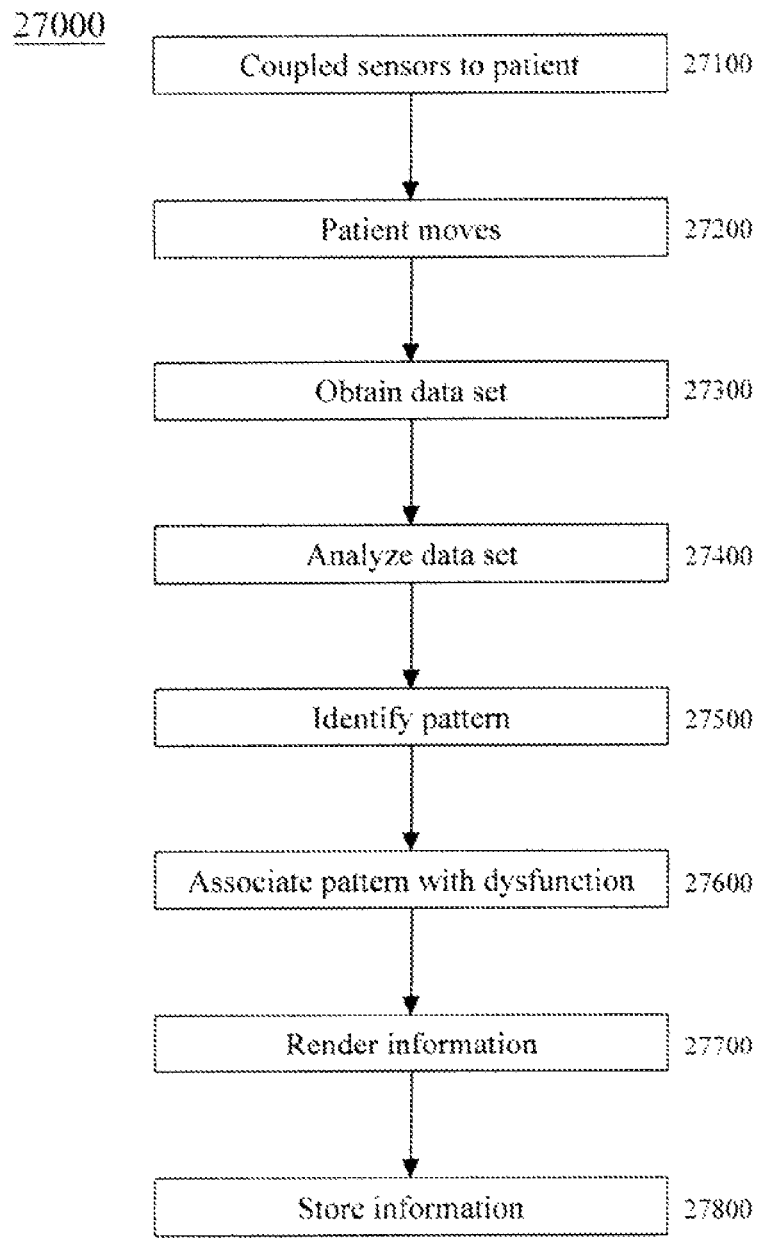
FIG. 27 is a block diagram of an exemplary embodiment of an information device 27000.

FIG. 27 is a flowchart of an exemplary embodiment of a method 27000. At activity 27100, biokinetographic sensors can be coupled to a patient. At activity 27200, the patient can move sufficiently to generate biokinetographic data, such as a biokinetographic data set. At activity 27300, the biokinetographic data set can be obtained, such as at an information device. At activity 27400, the biokinetographic data set can be analyzed, such as by determining a biokinetographic value for each biokinetographic variable in the biokinetographic data set. At activity 27500, a biokinetographic pattern can be identified, such as by comparing biokinetographic values to standards associated with the corresponding biokinetographic variables. At activity 27600, potentially using biokinetographic criteria and/or standards, the biokinetographic pattern can be associated with a specific dysfunction, such as Parkinson's disease, hemiparesis, cerebellar disease, frontal lobe disease, low pressure hydrocephalus, spinal stenosis, arthritis, orthopedic pain, orthopedic injury, motor neuropathy, myopathy, and/or a psychological dysfunction, such as depression, mania, anxiety, schizophrenia, hallucinations, delirium, etc. At activity 27700, information can be rendered, such as the biokinetographic data set; certain analytical information, such as values for biokinetographic variables such as heal strike, toe strike, heal liftoff, toe liftoff, single limb phase, double limb phase, swing phase, and/or opposite heal strike, etc.; arm swing character; stability of the center of mass, and/or step symmetry (degree of stability and/or equality between left and right steps), etc.; an identification of certain biokinetographic patterns; a comparison of certain biokinetographic values with certain biokinetographic criteria and/or standards; a diagnosis of a specific dysfunction; a treatment plan for a diagnosed dysfunction; and/or a prognosis for a diagnosed dysfunction. At activity 27800, any of the aforementioned information can be stored.

Certain exemplary embodiments can be useful as part of a comprehensive Health Promotion program (e.g., to set a target and/or to monitor progress), which can be useful for exercise monitoring, weight loss prescriptions, and/or mental stimulation. Certain exemplary embodiments can be useful as a method to improve function, such as balance and/or gait, to reduce arthritis pain, and/or to improve flexibility. Certain exemplary embodiments can be useful as a means to early self diagnosis.

Certain exemplary embodiments can be useful as a disease marker, such as for Alzheimer's disease, Parkinson's disease, diabetes mellitus, heart disease, chronic Lung disease, and/or malignancy, etc.

Certain exemplary embodiments can be useful as a functional marker, such as for falls and/or elective surgery, such as joint replacement (hip, knee, etc.), cataracts, bladder suspension, prostate, etc., medication trials (e.g., antidepressants, antihypertensives, diabetes medications, arthritis drugs, drugs for Alzheimer's and/or Parkinson's disease), and/or rehabilitation, such as physical therapy (back, hip, knee, etc.) and/or occupational therapy (shoulder, hands, activities of daily living, etc.), etc.

Certain exemplary embodiments can be useful for predicting recovery (improvement and/or risk of readmission to the hospital) after an acute illness, such as pneumonia, congestive heart failure, stroke, heart attack, fracture, delirium; healthcare utilization and/or policy; and/or optimal performance of elite athletes.

Certain exemplary embodiments can provide a system for detecting and analyzing the motion of a human subject, which can comprise: a plurality of sensors hooked to different moving parts of the subject; a recording device connected to the plurality of sensors, which acquires motion data generated from the plurality of sensors when the subject moves; a memory component installed in the recording device, which stores the motion data acquired by the recording device; and/or a processor configured to accept the motion data stored in the memory component, which converts the motion data into biokinetographic data.

Certain exemplary embodiments can provide the above system, wherein the sensors are biokinetic motion detectors.

Certain exemplary embodiments can provide the above system, wherein the sensors are biokinetic motion detectors that are wristwatch-sized triaxial piezo-resistive accelerometers that measure accelerations related to changes in velocity and gravitational acceleration.

Certain exemplary embodiments can provide the above system, wherein the subject wears the plurality of sensors on the wrists, neck, sacrum, and ankles while walking a closed course for generating motion data.

Certain exemplary embodiments can provide the above system, wherein the sensors are worn on the wrists and ankles by the subject and are attached by Velcro straps or other equivalent means.

Certain exemplary embodiments can provide the above system, wherein the plurality of sensors are attached to the recording device by wires or other equivalent means.

Certain exemplary embodiments can provide the above system, wherein the recording device is attached around the waist of the subject with a Theraband sash or other equivalent means.

Certain exemplary embodiments can provide the above system, wherein the recording device acquires motion data from the plurality of sensors by wireless or other remote means.

Certain exemplary embodiments can provide the above system, wherein the motion data is stored in individual channels of the memory component.

Certain exemplary embodiments can provide the above system, wherein the memory component is a removable memory card, chip, magnetic or other equivalent storage device.

Certain exemplary embodiments can provide the above system, wherein the biokinetographic data is in the format of waveforms or waveform images.

Certain exemplary embodiments can provide a method of detecting and analyzing the motion of a human subject, which can comprise: hooking a plurality of sensors to different moving parts of the subject; generating motion data from the plurality of sensors upon instructing the subject to move; recording motion data generated from the plurality of sensors; downloading the recorded motion data into a processing system; and/or converting the motion data into biokinetographic data.

Certain exemplary embodiments can provide the above method, wherein the plurality of sensors is tuned to a frequency in the range of 50 Hz to 250 Hz during the generation of motion data.

Certain exemplary embodiments can provide the above method, wherein the converting step comprises graphing the sum of vector magnitudes of acceleration from each sensor over time.

Certain exemplary embodiments can provide the above method, wherein the converting step comprises graphing the sum of vector magnitudes exhibit periodic waveforms that constitute biokinetographic signatures.

Each of the following U.S. Patents and U.S. Patent Application Publications are incorporated by reference herein in their entirety:

1. U.S. Pat. No. 6,834,436 entitled "Posture and body movement measuring system;"
2. U.S. Pat. No. 6,790,178 entitled "Physiological monitor and associated computation, display and communication unit;"
3. U.S. Pat. No. 6,491,647 entitled "Physiological sensing device;"
4. U.S. Pat. No. 6,433,690 entitled "Elderly fall monitoring method and device;"
5. U.S. Pat. No. 6,148,280 entitled "Accurate, rapid, reliable position sensing using multiple sensing technologies;"
6. U.S. Pat. No. 6,817,979 entitled "System and method for interacting with a user's virtual physiological model via mobile terminal;"
7. U.S. Pat. No. 6,551,252 entitled "Systems and methods for ambulatory monitoring of physiological signs;"
8. U.S. Pat. No. 6,703,939 entitled "System and method for detecting motion in a body;"
9. U.S. Pat. No. 6,513,381 entitled "Motion analysis system;"
10. U.S. Pat. No. 6,234,975 entitled "Non-invasive method of physiologic vibration quantification;"
11. U.S. Pat. No. 6,160,478 entitled "Wireless health monitoring system;"
12. U.S. Pat. No. 6,789,030 entitled "Portable data collector and analyzer: apparatus and method;"
13. U.S. Pat. No. 6,498,994 entitled "Systems and methods for determining energy experienced by a user and associated with activity;"
14. U.S. Pat. No. 6,282,441 entitled "Health monitoring system;"
15. U.S. Pat. No. 6,095,985 entitled "Health monitoring system;"
16. U.S. Pat. No. 5,778,882 entitled "Health monitoring system;"

17. U.S. Pat. No. 6,280,409 entitled "Medical for tracking patient functional status;"
18. U.S. Pat. No. 6,199,018 entitled "Distributed diagnostic system;"
19. U.S. Pat. No. 5,524,637 entitled "Interactive system for measuring physiological exertion;"
20. U.S. Patent Application Publication No. 20050010139 entitled "Body movement monitoring device;"
21. U.S. Patent Application Publication No. 20040015103 entitled "Body movement monitoring system and method;" and
22. U.S. Patent Application Publication No. 20030139692 entitled "Method for analyzing irregularities in human locomotion."

Definitions

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.
acceleration—the rate of change of velocity with respect to time.
activity—an action, act, step, and/or process or portion thereof.
adapted to—made suitable or fit for a specific use or situation.
and/or—either in conjunction with or in alternative to.
apparatus—an appliance or device for a particular purpose
arthritis—inflammation of a joint, usually accompanied by pain, swelling, and stiffness, and resulting from infection, trauma, degenerative changes, metabolic disturbances, and/or other causes. It occurs in various forms, such as bacterial arthritis, osteoarthritis, or rheumatoid arthritis.
associate—to relate.
automatically—acting or operating in a manner essentially independent of external influence or control. For example, an automatic light switch can turn on upon "seeing" a person in its view, without the person manually operating the light switch.
biokinetograph—a rendering of acceleration versus time, such as an amplitude of a single acceleration or a linear combination of amplitudes of a plurality of mutually-orthogonal accelerations, each acceleration measured at a predetermined location on a human anatomical member.
biokinetographic—a characteristic associated with and/or derived from biokinetograph, such as biokinetographic data and/or a biokinetographic pattern.
can—is capable of, in at least some embodiments.
cause—to bring about, compel, and/or result in.
cerebellar disease—any dysfunction of the cerebellum, which can include causes such as agenesis, von Hippel-Lindau disease, Arnold Chiari malformations, Dandy Walker malformation, multiple sclerosis, Friedreich's ataxia, Louis Barr syndrome—ataxia telangiectasia, abscess formation, acute cerebellaritis, acute disseminated encephalomyelitis, some variants of Guillain Barre syndrome, astrocytoma, medulloblastoma, haemangioblastoma, metastasis, myxoedema, alcohol/vitamin B1 deficiency, cerebellar haemorrhage, cerebellar infarction, anticonvulsants—phenytoin, other sedatives—antipsychotics, benzodiazepines, and/or alcohol, etc.
compare—to examine in order to note the similarities or differences of.
comparison—the act of comparing or the process of being compared.
comprising—including but not limited to.
corresponding—accompanying, related, and/or associated.
data—distinct pieces of information, usually formatted in a special or predetermined way and/or organized to express concepts.
data set—a group of related values.
define—to establish the outline, form, or structure of
determine—to obtain, calculate, decide, deduce, and/or ascertain.
device—a machine, manufacture, and/or collection thereof
diagnose—to determine, distinguish, or identify the nature and/or cause of
dysfunction—a disease, disorder, injury, abnormality, and/or impairment.
electromagnetic wave—a wave of energy having a frequency within the electromagnetic spectrum and propagated as a periodic disturbance of the electromagnetic field when an electric charge oscillates or accelerates and/or one of the waves that are propagated by simultaneous periodic variations of electric and magnetic field intensity and that include radio waves, infrared, visible light, ultraviolet, X rays, and gamma rays.
frontal lobe disease—any disease primarily affecting the frontal lobes, including stroke, frontal temporal lobe dementia, Pick's disease, cerebral artery infarction, front lobe degeneration, frontal lobe lesions, schizophrenia, etc.
group—a number of individuals or things considered together because of similarities.
haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.
hemiparesis—muscular weakness or partial paralysis restricted to one side of the body.
information device—any device capable of processing information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or a graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc.

input/output (I/O) device—any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.

machine instructions—directions adapted to cause a machine, such as an information device, to perform one or more particular activities, operations, or functions. The directions, which can sometimes form an entity called a "processor", "kernel", "operating system", "program", "application", "utility", "subroutine", "script", "macro", "file", "project", "module", "library", "class", and/or "object", etc., can be embodied as machine code, source code, object code, compiled code, assembled code, interpretable code, and/or executable code, etc., in hardware, firmware, and/or software.

machine readable medium—a physical structure from which a machine can obtain data and/or information. Examples include a memory, punch cards, etc.

may—is allowed and/or permitted to, in at least some embodiments.

memory device—an apparatus capable of storing analog or digital information, such as instructions and/or data. Examples include a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions adapted to be executed by processor, such as according to an embodiment disclosed herein.

method—a process, procedure, and/or collection of related activities for accomplishing something.

motor neuropathy—a disease or an abnormality of the nervous system, especially one affecting the nerves that transmit signals to the muscles enabling them to carry out movements like walking and moving the hands.

myopathy—any of various abnormal conditions or diseases of the muscular tissues, especially one involving skeletal muscle.

network—a communicatively coupled plurality of nodes. A network can be and/or utilize any of a wide variety of sub-networks, such as a circuit switched, public-switched, packet switched, data, telephone, telecommunications, video distribution, cable, terrestrial, broadcast, satellite, broadband, corporate, global, national, regional, wide area, backbone, packet-switched TCP/IP, Fast Ethernet, Token Ring, public Internet, private, ATM, multi-domain, and/or multi-zone sub-network, one or more Internet service providers, and/or one or more information devices, such as a switch, router, and/or gateway not directly connected to a local area network, etc.

network interface—any device, system, or subsystem capable of coupling an information device to a network. For example, a network interface can be a telephone, cellular phone, cellular modem, telephone data modem, fax modem, wireless transceiver, Ethernet card, cable modem, digital subscriber line interface, bridge, hub, router, or other similar device.

obtain—to get, acquire, take, receive, and/or determine.

orthogonal directions—at right angles.

orthopedic injury—an injury of the skeletal system and/or associated muscles, joints, and/or ligaments.

orthopedic pain—pain originating and/or associated with the skeletal system and/or associated muscles, joints, and/or ligaments.

overall health status—a general quantitative or qualitative measure of health.

Parkinson's disease—a degenerative disorder of the central nervous system characterized by tremor and impaired muscular coordination.

plurality—the state of being plural and/or more than one.

predetermined—established in advance.

processor—a device and/or set of machine-readable instructions for performing one or more predetermined tasks. A processor can comprise any one or a combination of hardware, firmware, and/or software. A processor can utilize mechanical, pneumatic, hydraulic, electrical, magnetic, optical, informational, chemical, and/or biological principles, signals, and/or inputs to perform the task(s). In certain embodiments, a processor can act upon information by manipulating, analyzing, modifying, converting, transmitting the information for use by an executable procedure and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein. prognosis—a prediction of the probable course and/or outcome of a dysfunction, and/or a likelihood of recovery from a dysfunction.

psychological dysfunction—any condition described in the Diagnostic and Statistical Manual of Mental Disorders (DSM-IV-TR) of the American Psychiatric Association.

render—make perceptible to a human, for example as data, commands, text, graphics, audio, video, animation, and/or hyperlinks, etc., such as via any visual, audio, and/or haptic means, such as via a display, monitor, electric paper, ocular implant, cochlear implant, speaker, etc.

repeatedly—again and again; repetitively.

result—a consequence of a particular action, operation, or course; an outcome.

scalar sum—an aggregate of amplitudes.

set—a related plurality.

signal—information, such as machine instructions for activities, encoded as automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc. Depending on the context, a signal can be synchronous, asynchronous, hard real-time, soft real-time, non-real time, continuously generated, continuously varying, analog, discretely generated, discretely varying, quantized, digital, continuously measured, and/or discretely measured, etc.

specific—explicit, definite, distinctive, and/or unique.

standard—an acknowledged measure of comparison for quantitative or qualitative value; a criterion.

store—to place, hold, and/or retain data, typically in a memory.

substantially—to a great extent or degree.

system—a collection of mechanisms, devices, data, and/or instructions, the collection designed to perform one or more specific functions.

treatment—an act, manner, or method of handling or dealing with someone or something.

user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

value—a measured, assigned, determined, and/or calculated quantity.

variable—a quantity capable of assuming any of a set of values.

via—by way of and/or utilizing.

Still other practical and useful embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. Thus, regardless of the content of any portion (e.g., title, field, background, summary, abstract, drawing figure, etc.) of this application, unless clearly specified to the contrary, such as via an explicit definition, assertion, or argument, with respect to any claim, whether of this application and/or any claim of any application claiming priority hereto, and whether originally presented or otherwise: there is no requirement for the inclusion of any particular described or illustrated characteristic, function, activity, or element, any particular sequence of activities, or any particular interrelationship of elements; any elements can be integrated, segregated, and/or duplicated; any activity can be repeated, performed by multiple entities, and/or performed in multiple jurisdictions; and any activity or element can be specifically excluded, the sequence of activities can vary, and/or the interrelationship of elements can vary. Moreover, when any number or range is described herein, unless clearly stated otherwise, that number or range is approximate. When any range is described herein, unless clearly stated otherwise, that range includes all values therein and all sub-ranges therein. For example, if a range of 1 to 10 is described, that range includes all values therebetween, such as for example, 1.1, 2.5, 3.335, 5, 6.179, 8.9999, etc., and includes all sub-ranges therebetween, such as for example, 1 to 3.65, 2.8 to 8.14, 1.93 to 9, etc.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

Accordingly, the descriptions and drawings are to be regarded as illustrative in nature, and not as restrictive.

What is claimed is:

1. One or more computer-storage media having computer-executable instructions embodied thereon that, when executed, perform a method for identifying a risk of falling for a unique patient based on comparison results for one or more biokinetographic values for one or more specific components of a gait cycle, the method comprising:

obtaining biokinetographic data for the unique patient;

identifying in said biokinetographic data one or more biokinetographic values for the one or more specific components of a gait cycle of the unique patient, wherein the specific components of the gait cycle are one or more of initiation of gait movement, base of gait, cadence, gait turnaround or arm swing during gait movement;

comparing each of the one or more biokinetographic values of the gait cycle of the unique patient to a corresponding standard of one or more specific dysfunctions for each of the one or more biokinetographic values of the gait cycle;

utilizing the comparison results for each of the one or more biokinetographic values of the gait cycle of the unique patient to determine one or more specific dysfunctions associated with the one or more biokinetographic values, wherein the comparison results are based on the comparison of each of the one or more biokinetographic values of the gait cycle of the unique patient to a corresponding standard of the one or more specific dysfunctions for each of the one or more biokinetographic values of the gait cycle; and identifying the risk of the unique patient falling based on the comparison results for each of the one or more biokinetographic values of the gait cycle of the unique patient when the biokinetographic value for the unique patient is slow cadence with less than 100 steps per minute or include a heel strike interval greater than 330 milliseconds, wherein the one or more biokinetographic values comprise magnitude of accelerations of less than one gravitational unit.

2. The media of claim 1, wherein the one or more biokinetographic values include 1) symmetrical cadence and 2) slow cadence.

3. The media of claim 1, wherein the specific dysfunction is arthritis.

4. The media of claim 1, wherein the specific dysfunction is myopathy.

5. The media of claim 1, wherein the specific dysfunction is motor neuropathy.

6. The media of claim 1, wherein the method further comprises diagnosing the specific dysfunction.

7. The media of claim 1, wherein the method further comprises assessing the specific dysfunction.

8. The media of claim 1, wherein the method further comprises determining a treatment for the specific dysfunction.

9. The media of claim 1, wherein the method further comprises providing a prognosis regarding the specific dysfunction.

* * * * *